US011295856B2

(12) United States Patent
LeBoeuf et al.

(10) Patent No.: US 11,295,856 B2
(45) Date of Patent: Apr. 5, 2022

(54) APPARATUS, SYSTEMS, AND METHODS FOR MEASURING ENVIRONMENTAL EXPOSURE AND PHYSIOLOGICAL RESPONSE THERETO

(71) Applicant: Valencell, Inc., Raleigh, NC (US)

(72) Inventors: Steven Francis LeBoeuf, Raleigh, NC (US); Jesse Berkley Tucker, Knightdale, NC (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 315 days.

(21) Appl. No.: 14/299,233

(22) Filed: Jun. 9, 2014

(65) Prior Publication Data
US 2014/0288396 A1 Sep. 25, 2014

Related U.S. Application Data

(60) Continuation of application No. 12/985,857, filed on Jan. 6, 2011, now abandoned, which is a division of
(Continued)

(51) Int. Cl.
*A61B 5/00* (2006.01)
*G16H 40/67* (2018.01)
(Continued)

(52) U.S. Cl.
CPC ........... *G16H 40/67* (2018.01); *A61B 5/0002* (2013.01); *A61B 5/0022* (2013.01); *A61B 5/02* (2013.01);
(Continued)

(58) Field of Classification Search
CPC ....... A61B 5/11; A61B 5/7203; A61B 5/0022; A61B 5/1455; A61B 5/618; G06F 19/3418; G06F 19/322; G06F 19/345
See application file for complete search history.

(56) References Cited

U.S. PATENT DOCUMENTS 3,595,219 A 7/1971 Friedlander et al.
4,240,882 A 12/1980 Ang et al.
(Continued)

FOREIGN PATENT DOCUMENTS

CN 101212927 A 7/2008
CN 201438747 U 4/2010
(Continued)

OTHER PUBLICATIONS

Wakeling, J. M. et al; "Modification of soft tissue vibrations in the leg by muscular activity"; J Appl Physiol.; 90:412-420.*
(Continued)

*Primary Examiner* — Lori A. Clow
*Assistant Examiner* — Marie Archer
(74) *Attorney, Agent, or Firm* — Myers Bigel, P.A.

(57) ABSTRACT

Apparatus, systems, and methods for measuring environmental exposure and physiological response thereto are provided. A monitoring apparatus worn by a subject includes a physiological sensor that detects physiological information from the subject, an environmental exposure sensor that detects at least one airborne analyte in a vicinity of the subject, and a processor. The processor processes signals produced by the environmental exposure sensor and calculates a volumetric concentration of the least one airborne analyte. In addition, the processor process signals produced by the at least one physiological sensor to determine a physiological response of the subject to the at least one airborne analyte. The apparatus also includes a motion sensor and the processor calculates a distance traveled by the subject via signals produced by the motion sensor and calculates a volume of air to which the subject has been exposed using the distance traveled by the subject.

21 Claims, 9 Drawing Sheets

Related U.S. Application Data application No. 11/848,878, filed on Aug. 31, 2007, now Pat. No. 8,157,730.

(60) Provisional application No. 60/905,761, filed on Mar. 8, 2007, provisional application No. 60/876,128, filed on Dec. 21, 2006, provisional application No. 60/875,606, filed on Dec. 19, 2006.

(51) Int. Cl.

| | |
|---|---|
| A61B 5/0205 | (2006.01) |
| A61B 5/11 | (2006.01) |
| A61B 5/145 | (2006.01) |
| G16H 40/63 | (2018.01) |
| G06Q 30/02 | (2012.01) |
| A61B 5/02 | (2006.01) |
| A63F 13/00 | (2014.01) |
| A61B 5/16 | (2006.01) |
| G16H 10/60 | (2018.01) |
| G16H 50/30 | (2018.01) |
| A61B 5/021 | (2006.01) |
| A61B 5/024 | (2006.01) |
| A61B 5/08 | (2006.01) |
| A61B 5/087 | (2006.01) |
| A61B 5/1455 | (2006.01) |
| A61B 5/026 | (2006.01) |

(52) U.S. Cl.
CPC ........ *A61B 5/0205* (2013.01); *A61B 5/02055* (2013.01); *A61B 5/11* (2013.01); *A61B 5/112* (2013.01); *A61B 5/1112* (2013.01); *A61B 5/1117* (2013.01); *A61B 5/1118* (2013.01); *A61B 5/14539* (2013.01); *A61B 5/14542* (2013.01); *A61B 5/14546* (2013.01); *A61B 5/165* (2013.01); *A61B 5/411* (2013.01); *A61B 5/415* (2013.01); *A61B 5/418* (2013.01); *A61B 5/486* (2013.01); *A61B 5/4812* (2013.01); *A61B 5/4848* (2013.01); *A61B 5/4866* (2013.01); *A61B 5/6802* (2013.01); *A61B 5/6803* (2013.01); *A61B 5/6815* (2013.01); *A61B 5/6817* (2013.01); *A61B 5/6887* (2013.01); *A61B 5/721* (2013.01); *A61B 5/7207* (2013.01); *A61B 5/742* (2013.01); *A63F 13/00* (2013.01); *G06Q 30/0241* (2013.01); *G06Q 30/0251* (2013.01); *G06Q 30/0269* (2013.01); *G06Q 30/0271* (2013.01); *G16H 10/60* (2018.01); *G16H 40/63* (2018.01); *G16H 50/30* (2018.01); *A61B 5/0059* (2013.01); *A61B 5/021* (2013.01); *A61B 5/024* (2013.01); *A61B 5/026* (2013.01); *A61B 5/02438* (2013.01); *A61B 5/087* (2013.01); *A61B 5/0816* (2013.01); *A61B 5/1455* (2013.01); *A61B 5/4064* (2013.01); *A61B 2505/07* (2013.01); *A61B 2560/0242* (2013.01); *A61B 2562/0219* (2013.01); *Y02A 90/10* (2018.01); *Y10S 128/92* (2013.01); *Y10S 707/99943* (2013.01)

(56) References Cited

U.S. PATENT DOCUMENTS

| | | |
|---|---|---|
| 4,331,154 A | 5/1982 | Broadwater et al. |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,952,890 A | 8/1990 | Swanson |
| 4,952,928 A | 8/1990 | Carroll et al. |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,113,869 A | 5/1992 | Nappholz et al. |
| 5,139,025 A | 8/1992 | Lewis et al. |
| 5,143,078 A | 9/1992 | Mather et al. |
| 5,226,417 A | 7/1993 | Swedlow et al. |
| 5,237,994 A | 8/1993 | Goldberger |
| 5,299,570 A | 4/1994 | Hatschek |
| 5,348,002 A | 9/1994 | Caro |
| 5,377,100 A | 12/1994 | Pope et al. |
| 5,431,170 A * | 7/1995 | Mathews ............. A61B 5/0002 600/323 |
| 5,448,082 A | 9/1995 | Kim |
| 5,482,036 A | 1/1996 | Diab et al. |
| 5,492,129 A | 2/1996 | Greenberger |
| 5,494,043 A | 2/1996 | O'Sullivan et al. |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,817,008 A | 10/1998 | Rafert et al. |
| 5,846,190 A | 12/1998 | Woehrle |
| 5,853,005 A | 12/1998 | Scanlon |
| 5,853,364 A | 12/1998 | Baker, Jr. et al. |
| 5,904,654 A | 5/1999 | Wohltmann et al. |
| 5,938,593 A | 8/1999 | Ouellette |
| 5,954,644 A | 9/1999 | Dettling et al. |
| 5,964,701 A | 10/1999 | Asada et al. |
| 5,971,930 A | 10/1999 | Elghazzawi |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Aceti et al. |
| 6,013,007 A | 1/2000 | Root et al. |
| 6,022,748 A | 2/2000 | Charych et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,155,983 A | 12/2000 | Kosuda et al. |
| 6,168,567 B1 | 1/2001 | Pickering et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,267,721 B1 | 7/2001 | Welles |
| 6,283,915 B1 | 9/2001 | Nolan et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |

(56) References Cited

U.S. PATENT DOCUMENTS

| | | |
|---|---|---|
| 6,371,925 B1 | 4/2002 | Imai et al. |
| 6,374,129 B1 | 4/2002 | Chin et al. |
| 6,393,311 B1 | 5/2002 | Edgar et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1* | 10/2002 | Brown ............... G06F 19/3406 600/300 |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,589,172 B2 | 7/2003 | Williams et al. |
| 6,605,038 B1 | 8/2003 | Teller et al. |
| 6,608,562 B1 | 8/2003 | Kimura et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,702,752 B2 | 3/2004 | Dekker |
| 6,725,072 B2 | 4/2004 | Steuer et al. |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,896,661 B2* | 5/2005 | Dekker ............... A61B 5/0205 600/300 |
| 6,941,239 B2 | 9/2005 | Unuma et al. |
| 6,953,435 B2 | 10/2005 | Kondo et al. |
| 6,954,644 B2 | 10/2005 | Johansson et al. |
| 6,996,427 B2 | 2/2006 | Ali et al. |
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Romhild |
| 7,034,694 B2 | 4/2006 | Yamaguchi et al. |
| 7,041,062 B2 | 5/2006 | Friedrichs et al. |
| 7,043,287 B1 | 5/2006 | Khalil et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,163,512 B1 | 1/2007 | Childre et al. |
| 7,175,601 B2 | 2/2007 | Verjus et al. |
| 7,190,986 B1 | 3/2007 | Hannula et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo et al. |
| 7,341,559 B2 | 3/2008 | Schultz et al. |
| 7,376,451 B2 | 5/2008 | Mahony et al. |
| 7,378,954 B2 | 5/2008 | Wendt |
| 7,470,234 B1 | 12/2008 | Elhag et al. |
| 7,483,730 B2 | 1/2009 | Diab et al. |
| 7,486,988 B2 | 2/2009 | Goodall et al. |
| 7,498,749 B2 | 3/2009 | Bruwer |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,620,450 B2 | 11/2009 | Kim et al. |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,679,008 B2 | 3/2014 | Hughes et al. |
| 8,730,048 B2 | 5/2014 | Shen et al. |
| 9,005,129 B2 | 4/2015 | Venkatraman et al. |
| 2001/0015123 A1 | 8/2001 | Nishitani et al. |
| 2001/0044588 A1 | 11/2001 | Mault |
| 2001/0049471 A1 | 12/2001 | Suzuki et al. |
| 2002/0035340 A1 | 3/2002 | Fraden et al. |
| 2002/0128931 A1 | 9/2002 | Geva |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0018821 A1 | 12/2002 | Aizawa |
| 2002/0186137 A1 | 12/2002 | Skardon |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0036683 A1 | 2/2003 | Kehr et al. |
| 2003/0036685 A1* | 2/2003 | Goodman ............ A61B 5/0002 600/300 |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1* | 4/2003 | Mault ............... A61B 5/02055 600/407 |
| 2003/0065269 A1* | 4/2003 | Vetter ............... A61B 5/02416 600/503 |
| 2003/0083583 A1 | 5/2003 | Kovtun et al. |
| 2003/0109030 A1 | 6/2003 | Uchida et al. |
| 2003/0109791 A1 | 6/2003 | Kondo et al. |
| 2003/0181795 A1 | 9/2003 | Suzuki et al. |
| 2003/0181798 A1 | 9/2003 | Al-Ali |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2003/0233051 A1 | 12/2003 | Verjus et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1* | 2/2004 | Kimball ............ A61B 5/14551 600/323 |
| 2004/0039254 A1* | 2/2004 | Stivoric ............ A61B 5/0205 600/300 |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |

(56) References Cited

U.S. PATENT DOCUMENTS

| | | |
|---|---|---|
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186387 A1 | 9/2004 | Kosuda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2004/0254501 A1 | 12/2004 | Mault |
| 2005/0004458 A1 | 1/2005 | Kanayama et al. |
| 2005/0007582 A1 | 1/2005 | Villers et al. |
| 2005/0021519 A1 | 1/2005 | Ghouri |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0036212 A1 | 2/2005 | Saito |
| 2005/0038349 A1 | 2/2005 | Choi et al. |
| 2005/0043600 A1 | 2/2005 | Diab et al. |
| 2005/0043630 A1 | 2/2005 | Honeyager et al. |
| 2005/0058456 A1* | 3/2005 | Yoo .............. A61B 5/7207 398/140 |
| 2005/0059870 A1 | 3/2005 | Aceti |
| 2005/0080322 A1* | 4/2005 | Korman .......... A61B 5/0006 600/300 |
| 2005/0084666 A1 | 4/2005 | Pong et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0212405 A1 | 9/2005 | Negley |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0228463 A1 | 10/2005 | Mac et al. |
| 2005/0240087 A1 | 10/2005 | Keenan et al. |
| 2005/0245839 A1 | 11/2005 | Stivoric et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0136173 A1* | 6/2006 | Case .............. A63B 24/00 702/182 |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0253010 A1* | 11/2006 | Brady ............ A61B 5/02438 600/324 |
| 2006/0264730 A1 | 11/2006 | Stivoric et al. |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1* | 3/2007 | Kil ................ A61K 49/00 705/3 |
| 2007/0060800 A1 | 3/2007 | Drinan et al. |
| 2007/0060819 A1 | 3/2007 | Altschuler et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0118054 A1 | 5/2007 | Oliver et al. |
| 2007/0123763 A1 | 5/2007 | Al-Ali et al. |
| 2007/0135717 A1 | 6/2007 | Uenishi et al. |
| 2007/0165872 A1 | 7/2007 | Bridger et al. |
| 2007/0167850 A1 | 7/2007 | Russell et al. |
| 2007/0173734 A1* | 7/2007 | Kim ................ A61B 5/04 600/546 |
| 2007/0191718 A1 | 8/2007 | Nakamura |
| 2007/0197878 A1* | 8/2007 | Shklarski ........ A61B 5/02055 600/300 |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0001735 A1 | 1/2008 | Tran |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0045806 A1 | 2/2008 | Keppler |
| 2008/0076972 A1 | 3/2008 | Dorogusker et al. |
| 2008/0081963 A1 | 4/2008 | Naghavi et al. |
| 2008/0081972 A1 | 4/2008 | Debreczeny |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0133699 A1 | 6/2008 | Craw et al. |
| 2008/0141301 A1 | 6/2008 | Azzaro et al. |
| 2008/0146890 A1 | 6/2008 | LeBoeuf et al. |
| 2008/0146892 A1 | 6/2008 | LeBoeuf et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221461 A1 | 9/2008 | Zhou et al. |
| 2008/0249594 A1 | 10/2008 | Dietrich |

(56) References Cited

U.S. PATENT DOCUMENTS

| | | | |
|---|---|---|---|
| 2008/0265170 A1* | 10/2008 | Ales | A61B 5/0059 250/372 |
| 2008/0287752 A1 | 11/2008 | Stroetz et al. | |
| 2009/0005662 A1 | 1/2009 | Petersen et al. | |
| 2009/0006457 A1 | 1/2009 | Stivoric et al. | |
| 2009/0010461 A1 | 1/2009 | Klinghult et al. | |
| 2009/0010556 A1 | 1/2009 | Uchibayashi et al. | |
| 2009/0030350 A1 | 1/2009 | Yang et al. | |
| 2009/0054751 A1 | 2/2009 | Babashan et al. | |
| 2009/0054752 A1 | 2/2009 | Jonnalagadda et al. | |
| 2009/0069645 A1 | 3/2009 | Nielsen et al. | |
| 2009/0082994 A1 | 3/2009 | Schuler et al. | |
| 2009/0088611 A1 | 4/2009 | Buschmann | |
| 2009/0093687 A1 | 4/2009 | Telfort et al. | |
| 2009/0105548 A1 | 4/2009 | Bart | |
| 2009/0105556 A1 | 4/2009 | Fricke et al. | |
| 2009/0112071 A1 | 4/2009 | LeBoeuf et al. | |
| 2009/0131761 A1 | 5/2009 | Moroney, III et al. | |
| 2009/0131764 A1 | 5/2009 | Lee et al. | |
| 2009/0175456 A1 | 7/2009 | Johnson | |
| 2009/0177097 A1 | 7/2009 | Ma et al. | |
| 2009/0214060 A1 | 8/2009 | Chuang et al. | |
| 2009/0221888 A1 | 9/2009 | Wijesiriwardana | |
| 2009/0227853 A1 | 9/2009 | Wijesiriwardana | |
| 2009/0240125 A1 | 9/2009 | Such et al. | |
| 2009/0253992 A1 | 10/2009 | Van Der Loo | |
| 2009/0253996 A1 | 10/2009 | Lee et al. | |
| 2009/0264711 A1 | 10/2009 | Schuler et al. | |
| 2009/0270698 A1 | 10/2009 | Shioi et al. | |
| 2009/0281435 A1 | 11/2009 | Ahmed et al. | |
| 2009/0287067 A1 | 11/2009 | Dorogusker et al. | |
| 2009/0299215 A1 | 12/2009 | Zhang | |
| 2010/0004517 A1 | 1/2010 | Bryenton et al. | |
| 2010/0022861 A1 | 1/2010 | Cinbis et al. | |
| 2010/0045663 A1 | 2/2010 | Chen et al. | |
| 2010/0100013 A1 | 4/2010 | Hu et al. | |
| 2010/0113948 A1 | 5/2010 | Yang et al. | |
| 2010/0168531 A1 | 7/2010 | Shaltis et al. | |
| 2010/0172522 A1 | 7/2010 | Mooring et al. | |
| 2010/0179389 A1 | 7/2010 | Moroney et al. | |
| 2010/0185105 A1 | 7/2010 | Baldinger | |
| 2010/0217102 A1 | 8/2010 | LeBoeuf et al. | |
| 2010/0217103 A1 | 8/2010 | Abdul-Hafiz et al. | |
| 2010/0222655 A1 | 9/2010 | Starr et al. | |
| 2010/0228315 A1 | 9/2010 | Nielsen | |
| 2010/0234714 A1 | 9/2010 | Mercier et al. | |
| 2010/0268056 A1 | 10/2010 | Picard et al. | |
| 2010/0274100 A1 | 10/2010 | Behar et al. | |
| 2010/0274109 A1 | 10/2010 | Hu et al. | |
| 2010/0292589 A1 | 11/2010 | Goodman | |
| 2010/0298653 A1 | 11/2010 | McCombie et al. | |
| 2011/0028810 A1 | 2/2011 | Van Slyke et al. | |
| 2011/0028813 A1 | 2/2011 | Watson et al. | |
| 2011/0081037 A1 | 4/2011 | Oh et al. | |
| 2011/0105869 A1 | 5/2011 | Wilson et al. | |
| 2011/0112382 A1 | 5/2011 | Li et al. | |
| 2011/0130638 A1 | 6/2011 | Raridan, Jr. | |
| 2011/0142371 A1 | 6/2011 | King et al. | |
| 2011/0288379 A1 | 11/2011 | Wu | |
| 2012/0030547 A1 | 2/2012 | Raptis et al. | |
| 2012/0095303 A1 | 4/2012 | He | |
| 2012/0156933 A1 | 6/2012 | Kreger et al. | |
| 2012/0179011 A1 | 7/2012 | Moon et al. | |
| 2012/0197093 A1 | 8/2012 | LeBoeuf et al. | |
| 2012/0277548 A1 | 11/2012 | Burton | |
| 2013/0053661 A1 | 2/2013 | Alberth et al. | |
| 2013/0072765 A1 | 3/2013 | Kahn et al. | |
| 2013/0131519 A1 | 5/2013 | LeBoeuf et al. | |
| 2013/0245387 A1 | 9/2013 | Patel | |
| 2013/0336495 A1 | 12/2013 | Burgett et al. | |
| 2014/0051940 A1 | 2/2014 | Messerschmidt | |
| 2014/0052567 A1 | 2/2014 | Bhardwaj et al. | |
| 2014/0073486 A1 | 3/2014 | Ahmed et al. | |
| 2014/0100432 A1 | 4/2014 | Golda et al. | |
| 2014/0127996 A1 | 5/2014 | Park et al. | |
| 2014/0219467 A1 | 8/2014 | Kurtz | |
| 2014/0236531 A1 | 8/2014 | Carter | |
| 2014/0275852 A1 | 9/2014 | Hong et al. | |
| 2014/0323880 A1 | 10/2014 | Ahmed et al. | |
| 2014/0378844 A1 | 12/2014 | Fei | |
| 2016/0287108 A1 | 10/2016 | Wei et al. | |
| 2017/0034615 A1 | 2/2017 | Mankodi et al. | |

FOREIGN PATENT DOCUMENTS

| | | |
|---|---|---|
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 20030159221 | 6/2003 |
| JP | 2004-513750 A | 5/2004 |
| JP | 2004-283523 | 10/2004 |
| JP | 2005-040261 A | 2/2005 |
| JP | 2005-270544 A | 10/2005 |
| JP | 2007-044203 | 2/2007 |
| JP | 2007-185348 | 7/2007 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 97/12544 A1 | 4/1997 |
| WO | WO 00/24064 | 4/2000 |
| WO | WO 00/47108 A1 | 8/2000 |
| WO | WO 01/08552 A1 | 2/2001 |
| WO | WO 02/17782 A2 | 3/2002 |
| WO | WO 2005/010568 A2 | 2/2005 |
| WO | WO 2005/020121 A1 | 3/2005 |
| WO | WO 2005/036212 A2 | 4/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/053146 A1 | 5/2007 |
| WO | WO 2008/141306 A2 | 11/2008 |
| WO | WO 2011/127063 A1 | 10/2011 |
| WO | WO 2013/038296 A1 | 3/2013 |

OTHER PUBLICATIONS

Kim, W. et al; "Measurement of the impulsive Bone Motion by Skin-Mounted Accelerometers"; Journal of Biomechanical Engineering, Feb. 23" vol. 115; p. 47-52.*

Lafortune, M. A.; "Tibial shock measured with bone and skin mounted transducers"; J. Biomechanics, vol. 28, No. 8, (1995), p. 989-993.*

Zhang, Q. et al; "Blood flow in the tibialis anterior muscle by photoplethysmography during foot-transmitted vibration"; Eur J Appl Physiol (2003) 90: 464-469 (Year: 2003).*

LeBlanc, J. A.; "Use of Heart Rate as an Index of Work Output"; J. Appl. Physiol. 10(2): 275-280 (1957) (Year: 1957).*

Pilcher, J. J. et al.; "Sleep quality versus sleep quantity: relationships between sleep and measures of health, well-being and sleepiness in college students"; J Psychosom Res, 42 (1997), pp. 583-596. (Year: 1997).*

Reddy, K. A. et al; "Motion Artifact Reduction in Photoplethysmographic Signals using Singular Value Descomposition"; Instrumentation and Measurement Technology conference—IMTC 2007; Warsaw, Poland, May 1-3, 2007; p. 1-4 (Year: 2007).*

Muzet, A.; "Environmental noise, sleep and health"; Sleep Medicine Reviews (2007) 11, 135-142 (Year: 2007).*

(56) References Cited

OTHER PUBLICATIONS

Widrow, B. et al; "Adaptive noise Cancelling: Principles and Applications"; Proceedings of the IEEE, vol. 63, No. 12, Dec. 1975; p. 1692-1716 (Year: 1975).*
A.A.R. Kamal, et al; "Skin photoplethysmography—a review"; Computer Methods and Programs in Biomedicine, vol. 28, Issue 4, 1989, pp. 257-269. (Year: 1989).*
Ebert, T et al., "Influence of Hydration Status on Thermoregulation and Cycling Hill Climbing," Med. Sci. Sport Exerc. Vol. 39, No. 2, pp. 323-329, 2007.
European Search Report corresponding to European Application No. 07862660.3 dated Apr. 25, 2012; 7 pages.
Falkner et al., "Cardiovascular response to mental stress in normal adolescents with hypertensive parents. Hemodynamics and mental stress in adolescents," Hypertension 1979, 1:23-30.
Fleming et al., "A Comparison of Signal Processing Techniques for the Extraction of Breathing Rate from the Photopethysmorgram," World Academy of Science, Engineering and Technology, vol. 30, Oct. 2007, pp. 276-280.
Geladas et al., "Effect of cold air inhalation on core temperature in exercising subjects under stress," The American Physiological Society, pp. 2381-2387, 1988.
International Search Report and Written Opinion of the International Searching Authority, corresponding to PCT/US2012/0948079, dated Oct. 9, 2012.
International Search Report and Written Opinion of the International Searching Authority, corresponding to PCT/US2007/025114, dated May 13, 2008.
International Search Report Corresponding to International Application No. PCT/US2012/022634, Date of Mailing: Aug. 22, 2012, 9 pages.
International Search Report corresponding to International Patent Application No. PCT/US2012/046446, Date of Mailing: Jan. 14, 2013, 3 pages.
Maughan et al., "Exercise, Heat, Hydration and the Brain," Journal of the American College of Nutrition, vol. 26, No. 5, p. 604S-612S, 2007.
Maughan, R.J., "Impact of mild dehydration on wellness and on exercise performance," European Journal of Clinical Nutrition, 57, Suppl. 2, pp. S19-S23, 2003.
Mostardi, R., et al., "The effect of increased body temperature due to exercise on the heart rate and the maximal aerobic power," Europ. J. Appl. Physiol, 33, pp. 237-245, 1974.
Nakajima et al., "Monitoring of heart and respiratory rates by photoplethyusmography using a digital filtering technique," Med. Eng. Phys., vol. 18, No. 5, Jul. 1996, pp. 365-372.
Notification of Transmittal of the International Search Report and Written Opinion of the International Search Authority dated Jul. 30, 2010 by the Korean Intellectual Property Office for corresponding International Application No. PCT/US2010/021936.
Notification of Transmittal of the International Search Report and Written Opinion of the International Search Authority dated Aug. 26, 2010 by the Korean Intellectual Property Office for corresponding International Application No. PCT/US2010/021629.
Notification of Transmittal of the International Search Report and the Written Opinion of the International Search Authority dated Sep. 16, 2010 by the Korean Intellectual Property Office for corresponding International Application No. PCT/US2010/024922.
Notification of Transmittal of the International Search Report and the Written Opinion of the International Search Authority dated Sep. 27, 2010 by the Korean Intellectual Property Office for corresponding International Application No. PCT/US2010/025216.
Notification of Transmittal of The International Search Report and The Written Opinion of the International Searching Authority, or the Declaration corresponding to International Application No. PCT/US2013/070271; dated Feb. 26, 2014; 13 pages.
Shorten et al., "Acute effect of environmental temperature during exercise on subsequent energy intake in active men," Am. J Clin. Nutr. 90, pp. 1215-1221, 2009.

Thompson, M.W., "Cardiovascular drift and critical core temperature: factors limiting endurance performance in the heat?" J. Exerc. Sci. Fit, vol. 4, No. 1, pp. 15-24, 2006.
Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.
European Search Report, EP Application No. 13863449.8, dated Oct. 19, 2015, 3 pages.
European Search Report, EP Application No. 14743615.8, dated Oct. 12, 2015, 3 pages.
European Search Report, EP Application No. 14743839.4, dated Oct. 12, 2015, 3 pages.
Gibbs et al., "Reducing Motion Artifact in Wearable Bio-Sensors Using MEMS Accelerometers for Active Noise Cancellation," 2005 American Control Conference, Jun. 8-10, 2005, Portland, Or, USA, pp. 1581-1586.
International Preliminary Report on Patentability, PCT/US2014/012940, dated Jun. 17, 2015, 23 pages.
International Search Report and Written Opinion of the International Searching Authority, corresponding to International Patent Application No. PCT/US2014/012940, dated Oct. 16, 2014,13 pages.
International Search Report corresponding to International Patent Application No. PCT/US2014/012909, dated May 13, 2014, 3 pages.
Notification Concerning Transmittal of International Preliminary Report on Patentability, PCT/US2014/012909, dated Jul. 28, 2015.
Notification of Transmittal of the International Search Report and the Written Opinion of the International Searching Authority, or the Declaration, PCT/US2015/014562, dated Oct. 28, 2015.
Notification of Transmittal of the International Search Report and the Written Opinion of the International Searching Authority, or the Declaration, PCT/US2015/042636, dated Oct. 29, 2015.
Notification of Transmittal of the International Search Report and the Written Opinion of the International Searching Authority, or the Declaration, PCT/US2015/042015, dated Oct. 29, 2015.
Notification of Transmittal of the International Search Report and the Written Opinion of the International Searching Authority, or the Declaration, PCT/US2015/042035, dated Oct. 29, 2015.
Wood et al., "Active Motion Artifact Reduction for Wearable Sensors Using Laguerre Expansion and Signal Separation," Proceedings of the 2005 IEEE Engineering in Medicine and Biology, 27th Annual Conference, Shanghai, China, Sep. 1-4, 2005, pp. 3571-3574.
Notification of Transmittal of the International Search Report and the Written Opinion of the International Searching Authority, or the Declaration, PCT/US2015/046079, dated Dec. 29, 2015.
Communication pursuant to Article 94(3) EPC, European Patent Application No. 13863449.8, dated Nov. 23, 2015, 7 pages.
Communication pursuant to Article 94(3) EPC, European Patent Application No. 14743615.8, dated Dec. 23, 2015, 7 pages.
Communication pursuant to Article 94(3) EPC, European Patent Application No. 14743839.4, dated Dec. 23, 2015, 6 pages.
Communication pursuant to Article 94(3) EPC, European Patent Application No. 12820308.0, dated Feb. 3, 2016, 5 pages.
Notification of Transmittal of the International Search Report and Written Opinion of the International Search Authority dated May 26, 2016 by the Korean Intellectual Property Office for corresponding International Application No. PCT/US2016/019126.
Notification of Transmittal of the International Search Report and Written Opinion of the International Search Authority dated May 26, 2016 by the Korean Intellectual Property Office for corresponding International Application No. PCT/US2016/019132.
Asada, et al., "Mobile Monitoring with Wearable Photoplethysmographic Biosensors," IEEE Engineering in Medicine and Biology Magazine, May/Jun. 2003, pp. 28-40.
Bifulco et al., "Bluetooth Portable Device for Continuous ECG and Patient Motion Monitoring During Daily Life," Medicon 2007, IFMBE Proceedings 16, 2007, pp. 369-372.
Brodersen et al., "In-Ear Acquisition of Vital Signs Discloses New Chances for Preventive Continuous Cardiovascular Monitoring,"

(56) References Cited

OTHER PUBLICATIONS

4th International Workshop on Wearable and Implantable Body Sensor Networks (BSN 2007), vol. 13 of the series IFMBE Proceedings, pp. 189-194.
Celka et al., "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.
Communication Pursuant to Article 94(3) EPC, EP 12 739 502.8, dated Jul. 19, 2016, 7 pages.
Communication Pursuant to Article 94(3) EPC, EP 14 743 615.8, dated Jul. 19, 2016, 7 pages.
Communication Pursuant to Article 94(3) EPC, EP 14 743 839.4, dated Jul. 20, 2016, 5 pages.
Comtois et al., "A Wearable Wireless Reflectance Pulse Oximeter for Remote Triage Applications," 2006 IEEE, pp. 53-54.
Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.
Duun et al., "A Novel Ring Shaped Photodiode for Reflectance Pulse Oximetry in Wireless Applications," IEEE Sensors 2007 Conference, pp. 596-599.
Geun et al., "Measurement Site and Applied Pressure Consideration in Wrist Photoplethysmography," The 23rd International Technical Conference on Circuits/Systems, Computersand Communications, 2008, p. 1 129-1132.
Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc, of SPIE, vol. 5765, pp. 811-819.
Haahr et al., "A Wearable "Electronic Patch" for Wireless Continuous Monitoring of Chronically Diseased Patients," Proceedings of the 5th International Workshop on Wearable and Implantable Body Sensor Networks, in conjunction with The 5th International Summer School and Symposium on Medical Devices and Biosensors, The Chinese University of Hong Kong, HKSAR, China, Jun. 1-3, 2008, pp. 66-70.
Jiang, Honghui, "Motion-Artifact Resistant Design of Photoplethysmograph Ring Sensor for Driver Monitoring," Thesis, Massachusetts Institute of Technology, Feb. 2004, 62 pages.
Kuzmina et al., "Compact multi-functional skin spectrometry set-up," Advanced Optical Materials, Technologies, and Devices, Proc, of SPIE, vol. 6596, 2007, p. 65960T-1 to 65960T-6.
Lee et al., "Respiratory Rate Detection Algorithms by Photoplethysmography Signal Processing," 30th Annual International IEEE Embs Conference, Vancouver, British Columbia, Canada, Aug. 20-24, 2008, pp. 1140-1143.
Lindberg et al., "Monitoring of respiratory and heart rates using a fibre-optic sensor," Med Biol Eng Comput, Sep. 1992, vol. 30, No. 5, pp. 533-537.
Luprano, Jean, "Sensors and Parameter Extraction by Wearable Systems: Present Situation and Future," pHealth 2008, May 21, 2008, 29 pages.
Lygouras et al., "Optical-Fiber Finger Photo-Plethysmograph Using Digital Techniques," IEEE Sensors Journal, vol. 2, No. 1, Feb. 2002, pp. 20-25.
Maguire et al., "The Design and Clinical Use of a Reflective Brachial Photoplethysmograph," Technical Report NUIM/SS/-/2002/04, Submitted Apr. 2002, Signals and Systems Research Group, National University of Ireland, Maynooth, Co. Kildare, Ireland, 13 pages.
Mendelson et al., "Measurement Site and Photodetector Size Considerations in Optimizing Power Consumption of a Wearable Reflectance Pulse Oximeter," Proceedings of the 25th Annual International Conference of the IEEE Embs, Cancun, Mexico, Sep. 17-21, 2003, pp. 3016-3019.
Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.
Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.
Renevey et al., "Wrist-Located Pulse Detection Using IR Signals, Activity and Nonlinear Artifact Cancellation," IEEE Embs, 2001,4 pages.
Rhee et al., "Artifact-Resistant Power-Efficient Design of Finger-Ring Plethysmographic Sensors," IEEE Transactions on Biomedical Engineering, vol. 4 8, No. 7, Jul. 2001, pp. 795-805.
Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.
Shin et al., "A Novel Headset with a Transmissive PPG Sensor for Heart Rate Measurement," ICBME 2008, Proceedings 23, 2009, pp. 519-522.
Spigulis et al., "Wearable wireless photoplethysmography sensors," Proc, of SPIE, vol. 6991, 2008, p. 699120-1 to 699120-7.
Takatani et al., "Optical Oximetry Sensors for Whole Blood and Tissue," IEEE Engineering in Medicine and Biology, Jun./Jul. 1994, pp. 347-357.
Vogel et al., "A System for Assessing Motion Artifacts in the Signal of a Micro-Optic In-Ear Vital Signs Sensor," 30th Annual International IEEE Embs Conference, Vancouver, British Columbia, Canada, Aug. 20-24, 2008.
Vogel et al., "In-Ear Heart Rate Monitoring Using a Micro-Optic Reflective Sensor," Proceedings of the 29th Annual International Conference of the IEEE Embs Cite Internationale, Lyon, France, Aug. 23-26, 2007, pp. 1375-1378.
Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.
Wang et al., "Reflective Photoplethysmograph Earpiece Sensor for Ubiquitous Heart Rate Monitoring," 4th International Workshop on Wearable and Implantable Body Sensor Networks, 2007, vol. 13 of the series IFMBE Proceedings, pp. 179-183.
Wei et al. "A New Wristband Wearable Sensor Using Adaptive Reduction Filter to Reduce Motion Artifact," Proceedings of the 5th International Conference on Information Technology and Application in Biomedicine, in conjunction with The 2nd International Symposium & Summer School on Biomedical and Health Engineering, Shenzhen, China, May 30-31, 2008, pp. 278-281.
Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.
Extended European Search Report, EP Application No. 16164775.5, dated Sep. 13, 2016, 7 pages.
Notification of Transmittal of International Preliminary Report on Patentability, PCT/US2015/041562, dated Oct. 20, 2016, 14 pages.
Notification of Transmittal of International Preliminary Report on Patentability, PCT/US2015/042636, dated Oct. 20, 2016, 7 pages.
Notification of Transmittal of International Preliminary Reporton Patentability, PCT/US2015/042015, dated Oct. 20, 2016, 10 pages.
Notification of Transmittal of International Preliminary Report on Patentability, PCT/US2015/042035, dated Oct. 20, 2016, 8 pages.
Notification of Transmittal of International Preliminary Report on Patentability, PCT/US2015/046079, dated Oct. 20, 2016, 10 pages.
Notification of Transmittal of the International Search Report and the Written Opinion of the International Searching Authority, or the Declaration, PCT/US2016/041842, dated Oct. 21, 2016, 5 pages.
Han et al., "Artifacts in wearable photoplethysmographs during daily life motions and their reduction with least mean square based active noise cancellation method," Computers in Biology and Medicine, 42, 2012, pp. 387-393.
Communication with Supplementary European Search Report, European Application No. 15830336.2, dated Jun. 7, 2017, 8 pp.
Comtois et al., "A Comparative Evaluation of Adaptive Noise Cancellation Algorithms for Minimizing Motion Artifacts in a

(56) References Cited

OTHER PUBLICATIONS

Forehead-Mounted Wearable Pulse Oximeter", *Proceedings of the 29$^{th}$ Annual International Conference of the IEEE EMBS*, Lyon, France, Aug. 23-26, 2007, pp. 1528-1531.

Han et al., "Development of a wearable health monitoring device with motion artifact reduced algorithm" *International Conference on Control, Automation and Systems 2007 (ICCAS 2007)*, Seoul, Korea, Oct. 17-20, 2007, pp. 1581-1584.

Kim et al., "Measurement of the Impulsive Bone Motion by Skin-Mounted Accelerometers", *Journal of Biomechanical Engineering*, vol. 115, Feb. 1993, pp. 47-52.

Lafortune et al., "Tibial Shock Measured With Bone and Skin Mounted Transducers", *J. Biomechanics*, vol. 28, No. 8, Aug. 1995 pp. 989-993.

Lee et al., "A Mobile Care System With Alert Mechanism", *IEEE Transactions On Information Technology In Biomedicine*, vol. 11, No. 5, Sep. 2007, pp. 507-517.

Wakeling et al., "Modification of soft tissue vibrations in the leg by muscular activity", *J. Appl. Physiol.*, vol. 90, No. 2, Feb. 1, 2001, pp. 412-420.

Webster, J. G. Design of Pulse Oximeters. IOP Publishing Ltd., 1997, Cover page, pp. i-xvi, pp. 34-159.

Rhee, Sokwoo. Design and analysis of artifact-resistive finger photoplethysmographic sensors for vital sign monitoring. Diss. Massachusetts Institute of Technology, 2000, p. 1-101.

"U.S. Army Fitness Training Handbook" by the Department of the Army, 2003, The Lyons Press, p. 17.

"Warfighter Physiological and Environmental Monitoring: A Study for the U.S. Army Research Institute in Environmental Medicine and the Soldier Systems Center", Massachusetts Institute of Technology Lincoln Laboratory, Final Report, November, 1st 2004, prepared for the U.S. Army under Air Force Contract F1962800C0002; approved for public release.pg • 1-101.

Anpo et al. "Photocatalytic Reduction of Co2 With H20 on Titanium Oxides Anchored within Micropores of Zeolites: Effects of the Structure of the Active Sites and the Addition of Pt" J. Phys. Chern. B, (1997) 101:2 6 32-2 63 6.

Brsan et al. "Understanding the fundamental principles of metal oxide based gas sensors; the example of CO sensing with SnO2 sensors in the presence of humidity" Journal of Physics: Condensed Matter T5R8T3R839 (2003).

Bott "Electrochemistry of Semiconductors" *Current Separations* 17(3):87-91.

Colligan, M. J. et al. in "The psychological effects of indoor air pollution", Bulletin of the New York Academy of Medicine, vol. 57, No. 10, Dec. 1981, p. 1014-1026.

De Paula Santos, U. et al., in "Effects of air pollution on blood pressure and heart rate variability: a panel study of vehicular traffic controllers in the city of Sao Paulo, Brazil", European Heart Journal (2005) 26, p. 193-200.

Falkner, B et al. "Cardiovascular Response to Mental Stress in Normal Adolescents with Hypertensive Parents Hemodynamics and Mental Stress in Adolescents", Hypertension 1979, #2336. 1:2 3-3 0.

Fitrainer "The Only Trainer You Need"; http://itami.com; Downloaded Feb. 26, 2010; © 2008 FiTriainer™; 2 pages.

Gold, D.R et al. in "Ambient Pollution and Heart Rate Variability", Circulation 2000, 40-442674273 101:12 67-127 3.

Maomao, W. et al. "Mobile ContextAware Game for the Next Generation" 2$^{nd}$ International Conference on Application and Development of Computer Games ADGOG 2003 (2003), p. 78-81.

Martins et al. "Zinc oxide as an ozone sensor" Journal of Applied Physics 96(SkT398 T4U8 (2004) 9 6 (3) : 13 9 8-14 0 8.

Saladin et al. "Photosynthesis of CH4 at a TiO2 Surface from Gaseous H20 and C02" J. Chern. Soc., Chern. Commun/ 533534(1995) 5 3 3-5 3 4.

Skubal et al. "Detection and identification of gaseous organics using a $TiO_2$ sensor" *Journal of Photochemistry and Photobiology A: Chemistry* (2002) 148:103-108.

Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 58, 2000, sponsored by SPIE, 10 pp.

Zhang et al. "Development of Chemical Oxygen Demand Online Monitoring System Based on a Photoelectrochemical Degradation Principle" *Environ. Sci. Technol.*, (2006), 40(7):2363-2368.

* cited by examiner

APPARATUS, SYSTEMS, AND METHODS FOR MEASURING ENVIRONMENTAL EXPOSURE AND PHYSIOLOGICAL RESPONSE THERETO

RELATED APPLICATION

This application is a continuation application of pending U.S. patent application Ser. No. 12/985,857, filed Jan. 6, 2011, which is a divisional application of U.S. patent application Ser. No. 11/848,878, filed Aug. 31, 2007, now U.S. Pat. No. 8,157,730, and which claims the benefit of and priority to U.S. Provisional Patent Application No. 60/905,761, filed Mar. 8, 2007, U.S. Provisional Patent Application No. 60/876,128, filed Dec. 21, 2006, and U.S. Provisional Patent Application No. 60/875,606, filed Dec. 19, 2006, the disclosures of which are incorporated herein by reference as if set forth in their entireties.

FIELD OF THE INVENTION

The present invention relates generally to health and, more particularly, to health monitoring.

BACKGROUND

There is growing market demand for personal health and environmental monitors, for example, for gauging overall health and metabolism during exercise, athletic training, dieting, and physical therapy. However, traditional health monitors and environmental monitors may be bulky, rigid, and uncomfortable—generally not suitable for use during daily physical activity. There is also growing interest in generating and comparing health and environmental exposure statistics of the general public and particular demographic groups. For example, collective statistics enable the healthcare industry and medical community to direct healthcare resources to where they are most highly valued. However, methods of collecting these statistics may be expensive and laborious, often utilizing human-based recording/analysis steps at multiple sites.

SUMMARY

In view of the above discussion, systems and methods for monitoring various physiological and environmental factors, as well as systems and methods for using this information for a plurality of useful purposes, are provided. According to some embodiments of the present invention, real-time, non-invasive health and environmental monitors include a plurality of compact sensors integrated within small, low-profile devices. Physiological and environmental data is collected and wirelessly transmitted into a wireless network, where the data is stored and/or processed. This information is then used to support a variety of useful methods, such as clinical trials, marketing studies, biofeedback, entertainment, and others.

Though the methods herein may apply broadly to a variety of form factors for a monitoring apparatus, in some embodiments of the invention an earpiece functions as a physiological monitor, an environmental monitor, and a wireless personal communicator. Because the ear region is located next to a variety of "hot spots" for physiological an environmental sensing—including the tympanic membrane, the carotid artery, the paranasal sinus, etc.—in some cases an earpiece monitor takes preference over other form factors. The earpiece can take advantage of commercially available open-architecture, ad hoc, wireless paradigms, such as Bluetooth®, Wi-Fi, or ZigBee® communication protocols. In some embodiments, a small, compact earpiece contains at least one microphone and one speaker, and is configured to transmit information wirelessly to a recording device such as, for example, a cell phone, a personal digital assistant (PDA), and/or a computer. The earpiece contains a plurality of sensors for monitoring personal health and environmental exposure. Health and environmental information, sensed by the sensors is transmitted wirelessly, in real-time, to a recording device, capable of processing and organizing the data into meaningful displays, such as charts. In some embodiments, an earpiece user can monitor health and environmental exposure data in real-time, and may also access records of collected data throughout the day, week, month, etc., by observing charts and data through an audio-visual display.

Each physiological sensor is configured to detect and/or measure one or more of the following types of physiological information: heart rate, pulse rate, breathing rate, blood flow, heartbeat signatures, cardio-pulmonary health, organ health, metabolism, electrolyte type and/or concentration, physical activity, caloric intake, caloric metabolism, blood metabolite levels or ratios, blood pH level, physical and/or psychological stress levels and/or stress level indicators, drug dosage and/or dosimetry, physiological drug reactions, drug chemistry, biochemistry, position and/or balance, body strain, neurological functioning, brain activity, brain waves, blood pressure, cranial pressure, hydration level, auscultatory information, auscultatory signals associated with pregnancy, physiological response to infection, skin and/or core body temperature, eye muscle movement, blood volume, inhaled and/or exhaled breath volume, physical exertion, exhaled breath physical and/or chemical composition, the presence and/or identity and/or concentration of viruses and/or bacteria, foreign matter in the body, internal toxins, heavy metals in the body, anxiety, fertility, ovulation, sex hormones, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, auscultatory information, response to external stimuli, swallowing volume, swallowing rate, sickness, voice characteristics, voice tone, voice pitch, voice volume, vital signs, head tilt, allergic reactions, inflammation response, auto-immune response, mutagenic response, DNA, proteins, protein levels in the blood, water content of the blood, pheromones, internal body sounds, digestive system functioning, cellular regeneration response, healing response, stem cell regeneration response, and/or other physiological information.

Each environmental sensor is configured to detect and/or measure one or more of the following types of environmental information: climate, humidity, temperature, pressure, barometric pressure, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy, optical radiation, X-rays, gamma rays, microwave radiation, terahertz radiation, ultraviolet radiation, infrared radiation, radio waves, atomic energy alpha particles, atomic energy beta-particles, gravity, light intensity, light frequency, light flicker, light phase, ozone, carbon monoxide, carbon dioxide, nitrous oxide, sulfides, airborne pollution, foreign material in the air, viruses, bacteria, signatures from chemical weapons, wind, air turbulence, sound and/or acoustical energy, ultrasonic energy, noise pollution, human voices, animal sounds, diseases expelled from others, exhaled breath and/or breath constituents of others, toxins from others, pheromones from others, industrial and/or transportation sounds, allergens, animal hair, pollen, exhaust from engines, vapors and/or fumes, fuel, signatures for mineral deposits and/or oil deposits, snow, rain, thermal energy, hot surfaces, hot gases, solar energy, hail, ice, vibrations, traffic, the number of people in a vicinity of the person, coughing and/or sneezing sounds from people in the vicinity of the person, loudness and/or pitch from those speaking in the vicinity of the person, and/or other environmental information.

In some embodiments, the signal processor is configured to process signals produced by the physiological and environmental sensors into signals that can be heard and/or viewed by the person wearing the apparatus. In some embodiments, the signal processor is configured to selectively extract environmental effects from signals produced by a physiological sensor and/or selectively extract physiological effects from signals produced by an environmental sensor.

A monitoring system, according to some embodiments of the present invention, may be configured to detect damage to a portion of the body of the person wearing the apparatus, and may be configured to alert the person when such damage is detected. For example, when a person is exposed to sound above a certain level that may be potentially damaging, the person is notified by the apparatus to move away from the noise source. As another example, the person may be alerted upon damage to the tympanic membrane due to loud external noises.

Information from the health and environmental monitoring system may be used to support a clinical trial and/or study, marketing study, dieting plan, health study, wellness plan and/or study, sickness and/or disease study, environmental exposure study, weather study, traffic study, behavioral and/or psychosocial study, genetic study, a health and/or wellness advisory, and an environmental advisory. The monitoring system may be used to support interpersonal relationships between individuals or groups of individuals. The monitoring system may be used to support targeted advertisements, links, searches or the like through traditional media, the internet, or other communication networks. The monitoring system may be integrated into a form of entertainments, such as health and wellness competitions, sports, or games based on health and/or environmental information associated with a user.

According to some embodiments of the present invention, a method of monitoring the health of one or more subjects includes receiving physiological and/or environmental information from each subject via respective portable monitoring devices associated with each subject, and analyzing the received information to identify and/or predict one or more health and/or environmental issues associated with the subjects. Each monitoring device has at least one physiological sensor and/or environmental sensor. Each physiological sensor is configured to detect and/or measure physiological information from the subject, and each environmental sensor is configured to detect and/or measure environmental conditions in a vicinity of the subject. The physiological information and/or environmental information may be analyzed locally via the monitoring device or may be transmitted to a location geographically remote from the subject for analysis. The collected information may undergo virtually any type of analysis. In some embodiments, the received information may be analyzed to identify and/or predict the aging rate of the subjects, to identify and/or predict environmental changes in the vicinity of the subjects, and to identify and/or predict psychological and/or physiological stress for the subjects.

According to some embodiments of the present invention, corrective action information may be communicated to the subjects in response to identifying one or more health and/or environmental problems associated with the subject. In addition or alternatively, corrective action information for the subjects may be communicated to third parties.

In some embodiments, a geographical map illustrating health-related and/or environmental conditions associated with the subjects may be created.

According to some embodiments of the present invention, a health and environmental monitoring system includes a plurality of portable monitoring devices, each comprising at least one physiological sensor and/or environmental sensor, a plurality of portable communication devices, wherein each communication device is in communication with a respective monitoring device and is configured to transmit data from the monitoring device to remote data storage, and a processor configured to analyze data within the remote data storage and to identify and/or predict health and/or environmental issues associated with each subject. Each physiological sensor is configured to detect and/or measure physiological information from a respective subject, and each environmental sensor is configured to detect and/or measure environmental conditions in a vicinity of the respective subject. Each monitoring device is configured to be worn by a respective subject (e.g., attached to a body of a respective subject, etc.). For example, a monitoring device may be configured to be attached to an ear of a respective subject.

In some embodiments, the processor is configured to communicate corrective action information to each respective subject. Corrective action information may be communicated to each subject via the monitoring device associated with each respective subject, or via other methods.

In other embodiments, the processor communicates corrective action information for a subject to a third party. The processor may be configured to perform various analyses including, but not limited to, identifying and/or predicting the aging rate of one or more subjects, identifying and/or predicting environmental changes in the vicinity of one or more subjects, and identifying and/or predicting psychological and/or physiological stress for one or more subjects. In some embodiments of the present invention, the processor is configured to create a geographical map illustrating health and/or environmental conditions associated with one or more subjects.

Information collected from each monitoring device may include information that is personal and private and information that can be made available to the public. As such, data storage, according to some embodiments of the present invention, may include a private portion and a public portion. In the private portion, health and environmental data that is personalized for each subject is stored. In the public portion, anonymous health and environmental data is stored and is accessible by third parties.

In other embodiments of the present invention, a method of delivering targeted advertising to a person includes collecting physiological and/or environmental information from the person, selecting an advertisement for delivery to the person based upon the collected physiological and/or environmental information, and delivering the selected advertisement to the person. The physiological and/or environmental information is collected via a monitoring device associated with the person and that includes at least one physiological sensor and/or environmental sensor, as described above. The received physiological and/or environmental information is analyzed to identify a physiological condition of the person and/or environmental condition in a vicinity of the person, and an advertisement is selected for a product or service related to an identified physiological and/or environmental condition. The selected advertisement can be delivered via any of various channels including, but not limited to, email, postal mail, television, radio, newspaper, magazine, the internet, and outdoor advertising.

According to some embodiments of the present invention, a system for delivering targeted advertising to people includes a plurality of portable monitoring devices, each comprising at least one physiological sensor and/or environmental sensor, as described above, and a remotely located advertisement selection device that receives physiological and/or environmental information from the monitoring devices, selects advertisements based upon the collected physiological and/or environmental information, and delivers selected advertisements to the monitored persons. The advertisement selection device receives physiological and/or environmental information from each monitoring device via a communication device (e.g., PDA, cell phone, laptop computer, etc.) associated with each respective monitoring device. In some embodiments, the advertisement selection device is configured to select an advertisement for a product and/or service related to a physiological condition of a person and/or for a product and/or service related to an environmental condition in a vicinity of a person.

In some embodiments, the advertisement selection device includes an ad server configured to deliver online advertisements. In other embodiments, the advertisement selection device includes an email server configured to deliver advertisements via email. In some embodiments, the advertisement selection device is configured to communicate with a third party service that can deliver selected advertisements via one or more of the following delivery channels: postal mail, television, radio, newspaper, magazine, the internet, and outdoor advertising.

According to some embodiments of the present invention, a method of supporting interpersonal relationships includes collecting physiological and/or environmental information from a monitoring device associated with a first person when the first person is in the presence of a second person, determining a stress level of the first person using the collected physiological and/or environmental information, and displaying the stress level to the first person. The monitoring device includes at least one physiological sensor and/or environmental sensor, as described above, and is configured to collect physiological and/or environmental information that includes indicators associated with stress experienced by the first person. The stress level of the first person may also be communicated to one or more third parties.

In some embodiments, the physiological and/or environmental information collected from the first person is analyzed to identify a source of stress. A solution for reducing stress also may be recommended to the first person. In some embodiments, the monitoring device can identify the second person.

According to some embodiments of the present invention, a system for supporting interpersonal relationships includes a portable monitoring device that collects physiological and/or environmental information from a first person when the first person is in the presence of a second person, and a processor that receives physiological and/or environmental information from the monitoring device. The processor determines a stress level of the first person using the collected physiological and/or environmental information, and transmits and/or displays the stress level to the first person. In some embodiments, the processor receives physiological and/or environmental information from the monitoring device via a communication device (e.g., PDA, cell phone, laptop computer, etc.) associated with the monitoring device. The processor may be configured to analyze the information and identify a source of stress. The processor may be configured to recommend solutions for reducing stress.

In another embodiment of the present invention, a method of supporting interpersonal relationships includes collecting physiological and/or environmental information from a monitoring device associated with a first person, and determining a mood of the first person using the collected physiological and/or environmental information. The collected information includes indicators associated with one or more moods of the first person. The mood of the first person may be communicated to a second person, for example, via a communication network (e.g., text message, email, voice message, etc.).

A system for supporting interpersonal relationships, according to other embodiments of the present invention, includes a portable monitoring device that collects physiological and/or environmental information from a first person, and a processor that receives physiological and/or environmental information from the monitoring device, and determines a mood of the first person using the collected physiological and/or environmental information. The processor receives physiological and/or environmental information from the monitoring device via a communication device (e.g., PDA, cell phone, laptop computer, etc.) associated with the monitoring device. The processor is configured to communicate the mood of the first person to a second person, for example, via a communication network (e.g., text message, email, voice message, etc.).

According to further embodiments of the present invention, a method of monitoring one or more subjects includes collecting physiological and/or environmental information from a monitoring device associated with each respective subject, storing the collected physiological and/or environmental information at a remote storage device, and comparing the stored physiological and/or environmental information with benchmark physiological and/or environmental information to identify at least one behavioral response of the one or more subjects. Behavioral responses may include, but are not limited to, behavioral responses to a product and/or service, behavioral responses to product and/or service marketing, behavioral responses to medical treatment, behavioral responses to a drug, etc.

According to some embodiments of the present invention, a system for monitoring one or more subjects includes a plurality of portable monitoring devices configured to collect physiological information from a subject and environmental condition information in a vicinity of a subject, as described above, and a processor that compares collected physiological and/or environmental information with benchmark physiological and/or environmental information to identify at least one behavioral response of the one or more subjects. As described above, behavioral responses may include, but are not limited to, behavioral responses to a product and/or service, behavioral responses to product and/or service marketing, behavioral responses to medical treatment, behavioral responses to a drug, etc. In some embodiments, a monitoring device may include a dosimeter configured to measure a dose of a drug taken by a respective subject.

According to further embodiments of the present invention, a method of monitoring patients, includes collecting physiological and/or environmental information from each patient via a monitoring device associated with each respective patient, and analyzing the collected information to determine caloric intake, health, and physical activity of each patient.

According to further embodiments of the present invention, an entertainment system includes a gaming device, and a plurality of portable, monitoring devices in communication with the gaming device, wherein each monitoring apparatus is associated with a game participant and is configured to transmit participant physiological information and/or environmental information wirelessly to the gaming device. The gaming device is configured to integrate into the gaming strategy physiological information and/or environmental information received from each monitoring apparatus. Each monitoring apparatus includes at least one physiological sensor and/or environmental sensor, as described above.

According to further embodiments of the present invention, a method of interacting with an electronic game includes collecting physiological and/or environmental information from a monitoring device associated with a person, analyzing the collected information to identify one or more health and/or environmental issues associated with the person, sending the identified one or more health and/or environmental issues to a gaming device, and incorporating the identified one or more health and/or environmental issues into a strategy of a game executing on the gaming device. The monitoring device includes at least one physiological sensor and/or environmental sensor, as described above.

In some embodiments, a gaming character may be created based on the person using the identified one or more health and/or environmental issues. In other embodiments, biofeedback may be provided to the person for improving at least one skill associated with the electronic game.

According to further embodiments of the present invention, a method of monitoring a participant in an activity includes collecting physiological and/or environmental information from a monitoring device associated with the participant, analyzing the collected physiological and/or environmental information to identify one or more health-related and/or environmental issues associated with the participant, and providing feedback to the participant, wherein the feedback is relevant to a skill utilized by the participant in the activity.

BRIEF DESCRIPTION OF THE DRAWINGS

FIGS. 5A-5B illustrates an earpiece module with an adjustable mouthpiece for monitoring physiological and environmental information near the mouth, according to some embodiments of the present invention, wherein FIG. 5A illustrates the mouthpiece in a stored position and wherein FIG. 5B illustrates the mouthpiece in an extended operative position.

DETAILED DESCRIPTION

Figure 1:
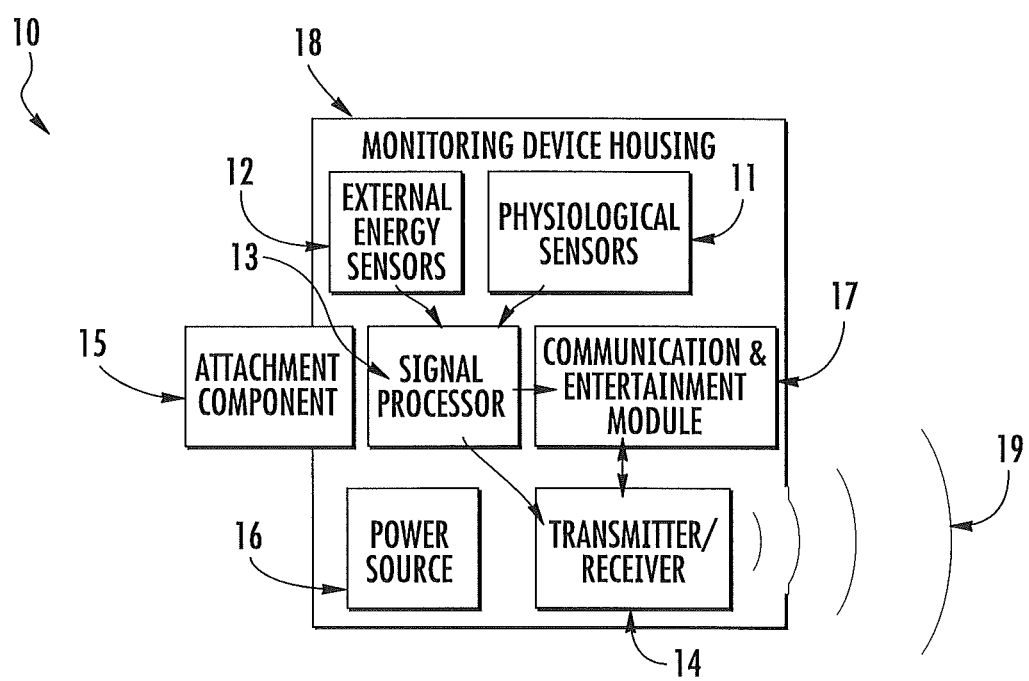
FIG. 1 is a block diagram of a telemetric monitoring device for physiological and/or environmental monitoring and personal communication, according to some embodiments of the present invention.

The present invention now is described more fully hereinafter with reference to the accompanying drawings, in which preferred embodiments of the invention are shown. This invention, however, may be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the sizes of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled"

with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "earpiece module" includes any type of device that may be attached to or near the ear of a user and may have various configurations, without limitation.

The term "real-time" is used to describe a process of sensing, processing, or transmitting information in a time frame which is equal to or shorter than the minimum timescale at which the information is needed. For example, the real-time monitoring of pulse rate may result in a single average pulse rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of an organism. However, in some cases, the term "psychological" is called-out separately to emphasize aspects of physiology that are more closely tied to conscious or subconscious brain activity rather than the activity of other organs, tissues, or cells.

The term "psychosocial stress" refers to events of psychological or social origin which challenge the homeostatic state of biological systems.

The term "body" refers to the body of a person (or animal) that may utilize an earpiece module according to embodiments of the present invention. Monitoring apparatus, according to embodiments of the present invention may be worn by humans and animals.

The term "health" refers generally to the quality or quantity of one or more physiological parameters with reference to an organism's functional abilities.

The term "ad hoc" refers generally to a wireless connection established for the duration of one session without the need for a base station. Instead, devices discover others within range to form a network. Bluetooth®, ZigBee®, and Wi-Fi communication protocols are a few examples.

The term "processor" refers to a device that takes one form of information and converts this information into another form, typically having more usefulness than the original form. For example, in this invention, a BLUECORE® processor may collect raw physiological or environmental data from various sensors and process this data into a meaningful assessment, such as pulse rate, blood pressure, or air quality. A variety of microprocessors or other processors may be used herein.

The term "clinical study" refers broadly to the application of science to health, where "health" may refer to both physical health as well as mental or psychological health. The term "clinical study" and "clinical trial" are used interchangeably herein. As an example, the interaction between a therapy and health or physiology—such as a drug therapy, exercise/diet plan, physical regime, etc.—can constitute a clinical study. As another example, the interaction between the health and the environmental exposure of individuals or groups can constitute a clinical study. In some cases a clinical study is performed by professionals in medicine or science. In other cases, a clinical study is performed by amateurs, computer programs, or individuals themselves, sometimes in the form of self help.

The term "marketing" refers to the act of bringing together buyers and sellers, and the term "marketing study" refers to the study of the needs and wants of buyers and sellers and how the buyers and sellers can come together.

The term "health study" refers to monitoring the health of an organism and studying the data regardless of the method of study.

The term "wellness" generally refers to a healthy balance of the mind-body and spirit that results in an overall feeling of well-being, and/or the state of being healthy. The term "wellness study" refers to the study of the quality of health and wellbeing. In some cases a wellness study is performed by professionals in medicine or science. In other cases, a clinical study is performed by amateurs, computer programs, or individuals themselves, sometimes in the form of self help.

The term "dieting plan" refers to a method of planning and/or regulating the intake of food or nutrients into the body. The term "exercise plan" refers to a method of planning or regulating physical activity. In many cases, a diet/exercise plan are used together to improve or reduce health. These plans can be operated by professionals, such as professional dieticians or physical trainers, or by amateurs. In some cases, these plans are regulated by computer programs or individuals themselves, sometimes in the form of self help.

The term "health study" refers to studying health as in its raw form, without necessarily being concerned about interactions between health and other factors.

The term "sickness and/or disease" refers generally to aspects of a sickness, disease, or injury in an individual or group of individuals.

The term "environmental exposure" refers to any environmental occurrence (or energy) to which an individual or group of individuals is exposed. For example, exposure to solar energy, air pollution, temperature, nuclear radiation, humidity, water, etc. may all constitute environmental exposure. A variety of relevant environmental energies are listed elsewhere herein.

In many cases, the above cases may overlap. As an example, a clinical study or wellness study may explore or record the interaction between physiological elements and environmental elements.

The term "aggregated" refers to information that is stored and/or grouped. In some cases, these groupings can be based on personal or demographical information, such as grouping based on ethnicity, sex, income, personal preferences or the like.

The terms "health and environmental network" and "health and environmental monitoring system" are used interchangeably herein. The terms "monitoring system" and "network" may be used interchangeably, as well.

The term "biofeedback" relates to measuring a subject's bodily processes such as blood pressure, heart rate, skin temperature, galvanic skin response (sweating), muscle tension, etc., and conveying such information to the subject in real-time in order to raise the subject's awareness and conscious control of the related physiological activities. Herein, biofeedback is synonymous with personal physiological monitoring, where biochemical processes and environmental occurrences may be integrated into information for one or more individuals. For example, monitoring hormone levels and air quality through the innovative sensor network described herein for the purpose of tracking, predicting, and/or controlling ovulation is also considered biofeedback.

The term "profile" relates to a summary of noteworthy characteristics and/or habits of an individual or group of individuals. These characteristics may be physiological (health-related), environmental, statistical, demographical, behavioral, and the like. Age, location, gender, sex, weight, ethnicity, and/or height may be included in a profile. Additionally, a profile may reference the buying and/or spending habits of an individual or group. Profiles may be utilized in making predictions about an individual or group.

The term "support," when used as a verb, means to assist and/or provide at least one method or outcome for something. For example, a method of supporting a therapy for something may refer to a method of assisting a therapeutic technique. In some cases, supporting a therapy may involve providing an entirely new method having a therapeutic outcome. As a more specific example, a noninvasive health and environmental monitor system/network may support a therapeutic drug study by noninvasively monitoring the real-time drug dosage in the body through multiwavelength pulse oximetry, monitoring core body temperature through thermal sensing of the tympanic membrane, and monitoring environments which may positively or negatively affect the quality of the drug therapy.

In the following figures, earpiece modules will be illustrated and described for attachment to the ear of the human body. However, it is to be understood that embodiments of the present invention are not limited to those worn by humans. Moreover, monitoring apparatus according to embodiments of the present invention are not limited to earpiece modules and/or devices configured to be attached to or near the ear. Monitoring apparatus according to embodiments of the present invention may be worn on various parts of the body or even worn inside the body.

Some embodiments of the present invention arise from a discovery that the ear is an ideal location on the human body for a wearable health and environmental monitor. The ear is a relatively immobile platform that does not obstruct a person's movement or vision. Devices located along the ear can have access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning). The ear is also at or near the point of exposure to: environmental breathable toxicants of interest (volatile organic compounds, pollution, etc.); noise pollution experienced by the ear; and lighting conditions for the eye. Located adjacent to the brain, the ear serves as an excellent location for mounting neurological and electrical sensors for monitoring brain activity. Furthermore, as the ear canal is naturally designed for transmitting acoustical energy, the ear provides an optimal location for monitoring internal sounds, such as heartbeat, breathing rate, and mouth motion.

Bluetooth®-enabled and/or other personal communication earpiece modules may be configured to incorporate physiological and/or environmental sensors, according to some embodiments of the present invention. Bluetooth® earpiece modules are typically lightweight, unobtrusive devices that have become widely accepted socially. Moreover, Bluetooth® earpiece modules are cost effective, easy to use, and are often worn by users for most of their waking hours while attending or waiting for cell phone calls. Bluetooth® earpiece modules configured according to embodiments of the present invention are advantageous because they provide a function for the user beyond health monitoring, such as personal communication and multimedia applications, thereby encouraging user compliance. Exemplary physiological and environmental sensors that may be incorporated into a Bluetooth® or other type of earpiece module include, but are not limited to accelerometers, auscultatory sensors, pressure sensors, humidity sensors, color sensors, light intensity sensors, pulse oximetry sensors, pressure sensors, etc.

Wireless earpiece devices incorporating low-profile sensors and other electronics, according to embodiments of the present invention, offer a platform for performing near-real-time personal health and environmental monitoring in wearable, socially acceptable devices. The capability to unobtrusively monitor an individual's physiology and/or environment, combined with improved user compliance, is expected to have significant impact on future planned health and environmental exposure studies. This is especially true for those that seek to link environmental stressors with personal stress level indicators. The large scale commercial availability of such low-cost devices can enable cost-effective large scale studies. The combination of monitored data with user location via GPS (Global Positioning System) and/or other location data can make on-going geographic studies possible, including the tracking of infection over large geographic areas. The commercial application of the proposed platform encourages individual-driven health maintenance and promotes a healthier lifestyle through proper caloric intake and exercise.

Embodiments of the present invention are not limited to devices that communicate wirelessly. In some embodiments of the present invention, devices configured to monitor an individual's physiology and/or environment may be wired to a device that stores, processes, and/or transmits data. In some embodiments, this information may be stored on the earpiece module itself.

FIG. 1 is a block diagram illustrating a wearable monitoring device 10, according to some embodiments of the present invention. The illustrated wearable monitoring device 10 includes one or more of the following: at least one physiological sensor 11, at least one environmental sensor 12 (also referred to as an external energy sensor), at least one signal processor 13, at least one transmitter/receiver 14, at least one power source 16, at least one communication & entertainment module 17, at least one body attachment component 15, and at least one housing 18. Though the health and environmental sensor functionality can be obtained without the communication and entertainment module 17, having this additional module may promote use of the wearable monitoring device 10 by users. The illustrated wearable monitoring device 10 is intended primarily for human use; however, the wearable monitoring device 10 may also be configured for use with other animals. In one preferred embodiment, the wearable monitoring device 10 is an earpiece module attached to the ear.

A physiological sensor 11 can be any compact sensor for monitoring the physiological functioning of the body, such as, but not limited to, sensors for monitoring: heart rate, pulse rate, breathing rate, blood flow, heartbeat signatures, cardio-pulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (drug dosimetry), physiological drug reactions, drug chemistry in the body, biochemistry, position & balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses & bacteria, foreign matter in the body, internal toxins, heavy metals in the body, anxiety, fertility, ovulation, sex hormones, psychological mood, sleep patterns, hunger & thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein levels in the blood, body hydration, water content of the blood, pheromones, internal body sounds, digestive system functioning, cellular regeneration response, healing response, stem cell regeneration response, and the like. Vital signs can include pulse rate, breathing rate, blood pressure, pulse signature, body temperature, hydration level, skin temperature, and the like. A physiological sensor may include an impedance plethysmograph for measuring changes in volume within an organ or body (usually resulting from fluctuations in the amount of blood or air it contains). For example, the wearable monitoring device 10 may include an impedance plethysmograph to monitor blood pressure in real-time.

An external energy sensor 12, serving primarily as an environmental sensor, can be any compact sensor for monitoring the external environment in the vicinity of the body, such as, but not limited to, sensors for monitoring: climate, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (optical radiation, X-rays, gamma rays, microwave radiation, terahertz radiation, ultraviolet radiation, infrared radiation, radio waves, and the like), EMF energy, atomic energy (alpha particles, beta-particles, gamma rays, and the like), gravity, light properties (such as intensity, frequency, flicker, and phase), ozone, carbon monoxide, greenhouse gases, CO2, nitrous oxide, sulfides, airborne pollution, foreign material in the air, biological particles (viruses, bacteria, and toxins), signatures from chemical weapons, wind, air turbulence, sound and acoustical energy (both human audible and inaudible), ultrasonic energy, noise pollution, human voices, animal sounds, diseases expelled from others, the exhaled breath and breath constituents of others, toxins from others, bacteria & viruses from others, pheromones from others, industrial and transportation sounds, allergens, animal hair, pollen, exhaust from engines, vapors & fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, other earpiece module users in the vicinity of the earpiece module user, coughing and sneezing sounds from people in the vicinity of the user, loudness and pitch from those speaking in the vicinity of the user, and the like.

In some embodiments, a physiological sensor 11 and/or an environmental sensor 12 may be configured to identify a person, such as biometric identification of a person, to whom the wearable monitoring device 10 is attached (or may be configured to identify other persons in the vicinity of the person wearing the monitoring device 10).

In some embodiments, a physiological sensor 11 and/or an environmental sensor 12 may be configured to monitor physical aging rate of a person or subject. The signal processor 13 may be configured to process information from a physiological sensor and/or an environmental sensor to assess aging rate. Physiological sensors configured to assess aging rate may include pulse rate sensors, blood pressure sensors, activity sensors, and psychosocial stress sensors. Environmental sensors configured to assess aging rate may include UV sensors and pollution sensors.

In some embodiments, a physiological sensor 11 and/or an environmental sensor 12 may be configured to be regenerated through a physical and/or chemical change. For example, it is anticipated that a wearable monitoring device 10, or other device incorporating physiological and/or environmental sensors according to embodiments of the present invention, may be coupled to an apparatus that is configured to "recharge" or regenerate one or more environmental and/or physiological sensors via a physical process or a chemical process, etc. For example, a recharging module for recharging electric power to the wearable monitoring device 10 may also user electrical energy to reverse a chemical or physical change in one of the sensors. One example of such a sensor would be a sensor that requires the absorption or desorption of water vapor for resetting to baseline operation. Another example is a sensor that is reset (recharged) through oxidation or reduction in order to change the surface properties for monitoring vapors, such as some metal oxide sensors.

Because the wearable monitoring device 10 is capable of measuring and transmitting sensor information in real-time over a duration of time, the physiological and environmental sensors 11, 12 can be used to sense the aforementioned parameters over time, enabling a time-dependent analysis of the user's health and environment as well as enabling a comparison between the user's health and environment. Combined with proximity or location detection, this allows an analysis for pinpointing the location where environmental stress and physical strain took place.

Proximity detection can be accomplished through GPS type devices integrated into the monitoring device 10 or a personal communication device in communication with the monitoring device 10. Proximity detection can also be accomplished through triangulation of wireless signals; if a cellular phone is used as the personal communication device (such as 21 of FIG. 2), proximity can be identified through existing cellular infrastructure for identifying the time and location of a phone call.

The signal processor 13 provides a means of converting the digital or analog signals from the sensors 11, 12 into data that can be transmitted wirelessly by the transmitter 14. The signal processor 13 may be composed of, for example, signal conditioners, amplifiers, filters, digital-to-analog and analog-to-digital converters, digital encoders, modulators, mixers, multiplexers, transistors, various switches, microprocessors, or the like. For personal communication, the signal processor 13 processes signals received by the receiver 14 into signals that can be heard or viewed by the user. The received signals may also contain protocol information for linking various telemetric modules together, and this protocol information can also be processed by the signal processor 13.

The signal processor 13 may utilize one or more compression/decompression algorithms (CODECs) used in digital media for processing data. The transmitter 14 can be comprised of a variety of compact electromagnetic transmitters. A standard compact antenna is used in the standard Bluetooth® headset protocol, but any kind of electromagnetic antenna suitable for transmitting at human-safe electromagnetic frequencies may be utilized. The receiver 14 can also be an antenna. In some embodiments, the receiving antenna and the transmitting antenna are physically the same. The receiver/transmitter 14 can be, for example, a non-line-of-sight (NLOS) optical scatter transmission system. These systems typically use short-wave (blue or UV) optical radiation or "solar blind" (deep-UV) radiation in order to promote optical scatter, but IR wavelengths can also suffice.

Additionally, a sonic or ultrasonic transmitter can be used as the receiver/transmitter 14 of the wearable monitoring device 10, but preferably using sounds that are higher or lower than the human hearing range. A variety of sonic and ultrasonic receivers and transmitters are available in the marketplace and may be utilized in accordance with embodiments of the present invention. If a telecommunication device 21 (FIG. 2) receiving wireless data signal 19 from the wearable monitoring device 10 is in close proximity to the wearable monitoring device 10, and the wearable module is an earpiece module, a variety of transmission schemes can be used. For communicating audible conversational information directly to the earpiece user, encoded telemetric conversational data received by the receiver 14 can be decoded by the signal processing module 13 to generate an electrical signal that can be converted into audible sound by the communication module 17.

In some embodiments, the transmitter/receiver 14 is configured to transmit signals from the signal processor to the remote terminal following a predetermined time interval. For example, the transmitter may delay transmission until a certain amount of detection time has elapsed, until a certain amount of processing time has elapsed, etc. In some cases, the transmitter/receiver 14 is configured to transmit signals to the remote terminal dependent on information sensed by the sensors 11, 12. For example, if an unstable pulse rate is sensed, a warning message may be sent to a remote terminal to communicate a need for help at a particular location.

The power source can be any portable power source 16 capable of fitting inside the housing 18. According to some embodiments, the power source 16 is a portable rechargeable lithium-polymer or zinc-air battery. Additionally, portable energy-harvesting power sources can be integrated into the wearable monitoring device 10 and can serve as a primary or secondary power source. For example, a solar cell module can be integrated into the wearable monitoring device 10 for collecting and storing solar energy. Additionally, piezoelectric devices or microelectromechanical systems (MEMS) can be used to collect and store energy from body movements, electromagnetic energy, and other forms of energy in the environment or from the user himself. A thermoelectric or thermovoltaic device can be used to supply some degree of power from thermal energy or temperature gradients. In some embodiments, a cranking or winding mechanism can be used to store mechanical energy for electrical conversion or to convert mechanical energy into electrical energy that can be used immediately or stored for later.

The various components described above are configured to fit within the wearable monitoring device housing 18 and/or be attached thereto. In the case where the wearable monitoring device 10 is an earpiece module, the housing 18 may be formed from any safe and comfortable solid material, such as metal, rubber, wood, polymers, ceramic, organic materials, or various forms of plastic. The body attachment component 15 is attached to the housing 18 and is designed to fit around or near the ear. For example, the standard Bluetooth® headset includes an earpiece attachment that is connected to the headset housing via a double-jointed socket, to provide comfort and positioning flexibility for the user. In some embodiments, the body attachment component 15 can be part of the housing 18, such that the entire earpiece module is one largely inflexible, rigid unit. In such case, a counterweight may be incorporated into the wearable monitoring device 10 to balance the weight of the earpiece electronics and power source. In some embodiments, the body attachment component 15 can contain physiological and environmental sensors, and the body attachment component 15 may be detachable. In some embodiments, more than one earpiece attachment 15 can be attached to the housing 18.

Figure 2:
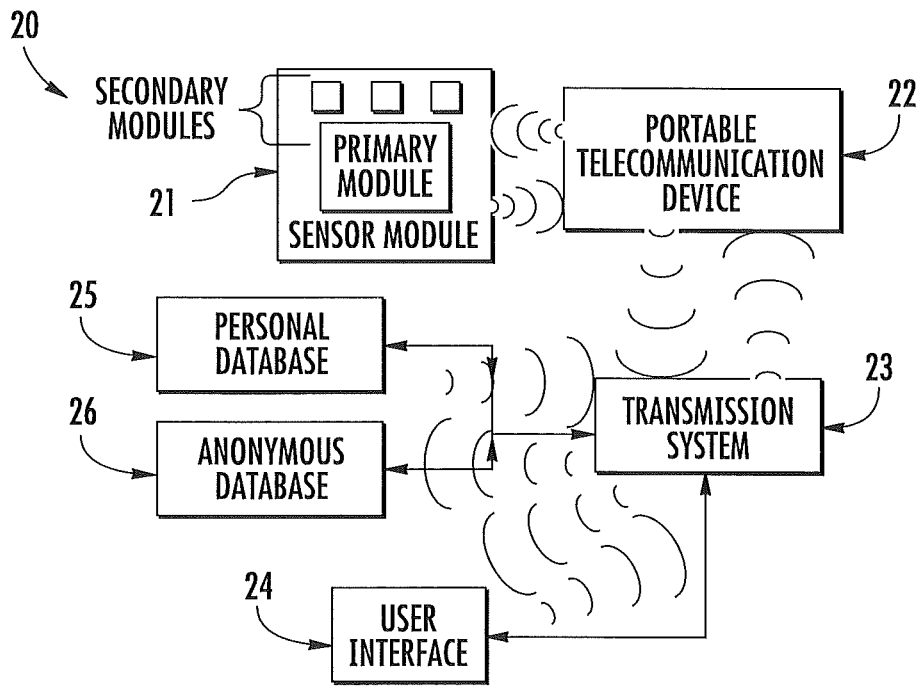
FIG. 2 is a block diagram of a telemetric network for health and environmental monitoring through portable telemetric monitoring devices, such as the device of FIG. 1, according to some embodiments of the present invention.

The communication and entertainment module 17 (also interchangeably referred to as a "communication module") is used for, but not limited to: processing or generating an audible sound from information received via the receiver 14 (from a cell phone, computer, network, database, or the like) and/or processing or generating an electrical signal from an audible sound from the user such that the electrical signal can be transmitted telemetrically via the transmitter 14. For example, in standard Bluetooth® protocol, communication electronics are used to convert an audible conversation into an electrical signal for telemetric conversation; communication electronics are also used to convert a digitized telemetric conversation into an audible conversation for the earpiece user. Additionally, the communication and entertainment module 17 can be used to store, process, or play analog or digital information from music, radio shows, videos, or other audible entertainment and to communicate this information to an earpiece user. In many cases, this information includes information received by the receiver 14. In many cases, the analog or digital information is not stored in the communication and entertainment module 17 but, rather, is stored in a portable telecommunication device 21 (FIG. 2). In such case, the communication and entertainment module 17 is used for converting the analog or digital information into audible sound for the earpiece user. The communication and entertainment module 17 may contain at least one microphone, speaker, signal processor (similar to 13), and digital memory. In some embodiments, the communication and entertainment module 17 may apply at least one CODEC for encoding or decoding information. The communication and entertainment module may utilize non-audible forms of communication with the user, such as visual, physical, or mental (i.e., brainwaves or neural stimulation) communication with the user.

In some embodiments, an audible communicator is provided that is configured to communicate therapeutic sounds (e.g., music therapy, etc.) to a person in response to physiological or psychosocial stress. The audible communicator may be embodied in the communication and entertainment module 17 or may be a separate speaker. In some embodiments, light therapy may be provided to a person in response to physiological or psychosocial stress. In some embodiments, the communication and entertainment module 17 may be configured to communicate a treatment, therapy, and/or plan of action to the person upon detection of physiological and/or environmental concerns. For example, if it is detected that the person is being exposed to unhealthy doses of UV radiation, the communication and entertainment module 17 may audibly instruct the person to move away from the person's current location (e.g., move indoors, etc.). Mechanical vibrational therapy and electrical stimulation therapy are also examples of automated therapies that may be invoked by programs inside the monitoring device 10 in response to sensor readings from health 11 and/or environmental 12 sensors.

Like the other components of the wearable monitoring device 10 shown in FIG. 1, the components of the communication and entertainment module 17 are not necessarily located in the same physical vicinity. The microphone and speaker of the communication module 17, for example, may be located closer to the mouth and ear respectively. Furthermore, the signal processor 13 can be composed of several components located throughout the earpiece module. It should be understood that the word "module" does not necessarily imply a unified physical location. Rather, "module" is used to imply a unified function.

Bluetooth® devices conventionally contain a communication module, such as communication module 17, for converting digital or analog information into audible sounds for the user. However, when combined with the health and environmental monitoring properties of a wearable monitoring device 10 according to embodiments of the present invention, the communication and entertainment module 17 can provide functionality. For the wearable monitoring device 10 can serve as a biofeedback device. As a non-limiting example, if a user is in a polluted environment, such as air filled with VOCs, the communication module 17 may notify the user to move to a new environment. As another example, if one or more of the physiological and environmental sensors 11, 12 of the wearable monitoring device 10 pick up a high particulate density in the environment, with an elevation in core body temperature, and a change in voice pitch occurring simultaneously (or near-simultaneously) within a common timeframe, the communication module 17 may alert the user that he/she may be having an allergic response. As a further example, the user can use the communication and entertainment module 17 to execute biofeedback for willfully controlling blood pressure, breathing rate, body temperature, pulse rate, and the like. The communication module 17 may utilize audible or visible alerts if the user is meeting their physiological targets or exceeding safe physiological limits. Alerting a user by physical or electrical force, such as the sense of touch or tingling from an electric pulse or vibration, can also be utilized. Thus, although communication by audible means is often utilized, the communication module 17 can alert, signify, or communicate with the user through sound, light, electrical actuation, and physical actuation.

Figure 9:
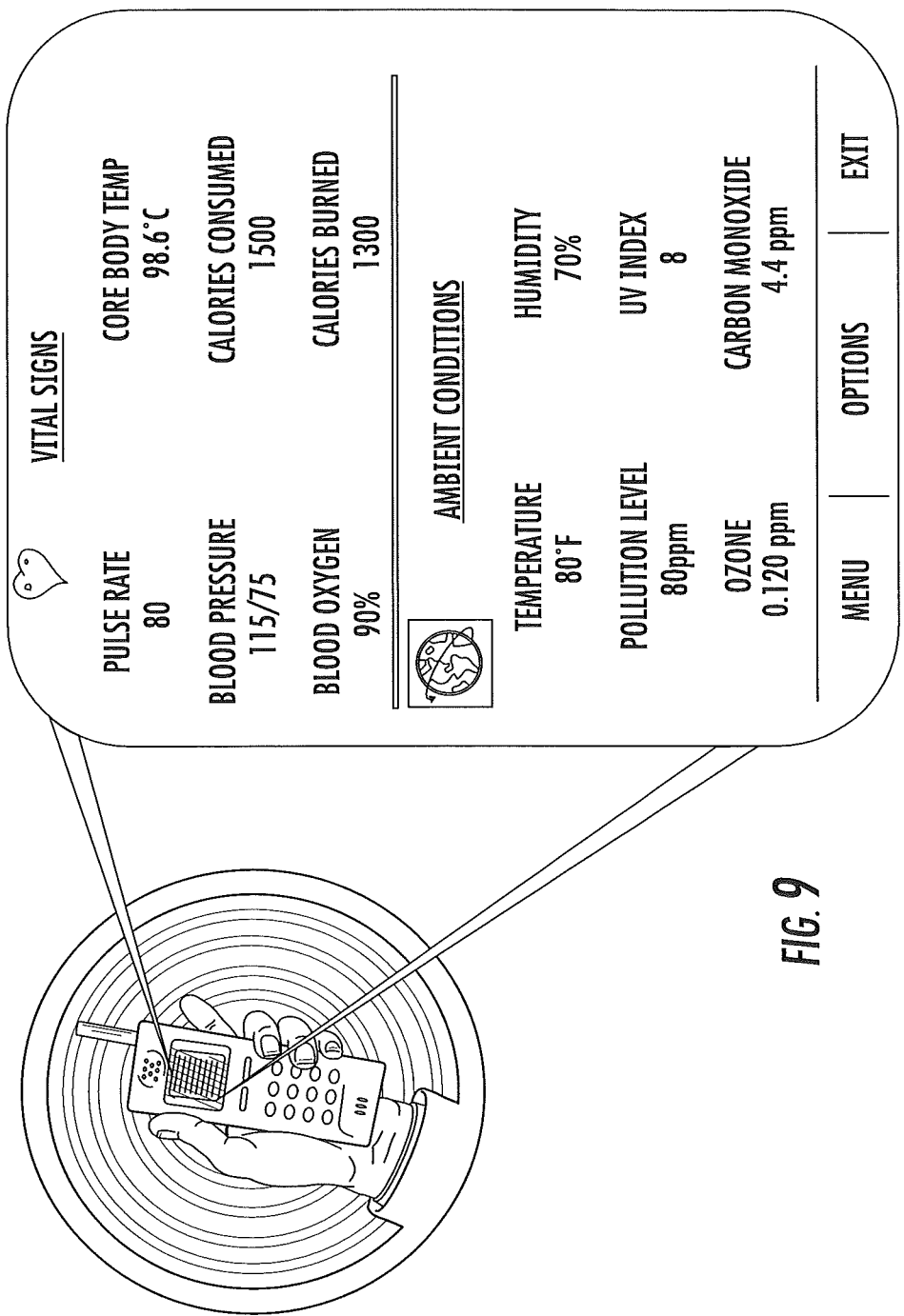
FIG. 9 illustrates the display of physiological and environmental information collected by a monitoring device, according to some embodiments of the present invention.

As a second example of this biofeedback method, basic vital signs collected by the physiological sensors 11 and processed by the signal processor 13 can be presented to the monitoring device user audibly, through the communication and entertainment module 17. For example, the user may be able to listen to his/her breathing rate, pulse rate, and the like. Additionally, an entertaining or aggravating sound or song can be used to alert the user to favorable or unfavorable personal health and environmental factors occurring in real-time. This technique may be applied towards education, such as positive or negative feedback for educational games, learning games, or games of deception (e.g., poker, etc.). FIG. 9 illustrates the display of physiological information and environmental information collected by a monitoring device 10 via a user's cell phone, according to some embodiments of the present invention.

In some embodiments, the wearable monitoring device 10 may be configured to deliver and/or monitor drugs, as in a dosimeter. For example, a transdermal drug delivery system may be provided that is controlled by monitoring device 10 electronics. Physiological sensors 11 can monitor the drug dosage and the physiological effects of the drug in real-time.

A health and environmental monitoring system 20 according to embodiments of the present invention that may incorporate wearable monitoring devices 10 of FIG. 1 is illustrated in FIG. 2. Other types of wearable monitoring devices may also be utilized in the health and environmental monitoring system 20. The wearable monitoring device 10 is utilized as a specific monitoring device 21 of the monitoring system 20, though other modules located at various other parts of the body can be used in conjunction with, or in place of, the wearable monitoring device 10. The terms "wearable monitoring device" and "sensor module" are used interchangeably herein in accordance with various embodiments of the present invention. The health and environmental monitoring system 20 is composed of at least one sensor module 21 (e.g., wearable monitoring device 10) at least one portable telecommunication module 22, at least one transmission system 23, at least one user interface 24, at least one personal database 25, and at least one anonymous database 26.

The sensor module 21 can be composed of a primary module alone or a primary module and at least one secondary module. The primary and secondary modules can be located at any location of the body, but in many cases it is preferable to be located in a region at or near the ear, and preferably the wearable monitoring device 10 serves as the primary module. In many cases, the secondary modules are not necessary. But in some cases, secondary modules may be located, for example, behind the ear (near the lymph nodes), at or near the earlobes (such as one or more earrings or ear clips), at the front of the ear (near the carotid artery), at the temples, along the neck, or other locations near the ear. In some cases the secondary modules, as with the primary module, can be located inside the body. These wearable secondary modules can be connected with either a "hard" connection to the primary module (such as an electric cable) or a "soft" connection to the primary module (such as a wireless connection). In Bluetooth® protocol, each secondary module can be simultaneously in direct wireless communication with the primary module. Primary modules and secondary modules in the same location can promote quick-donning, ease-of-use, and comfortability for the end user. Users may not be prone to accept multiple modules at multiple locations of the body.

The wearable sensor module 21 communicates wirelessly with the portable telecommunication device 22, preferably in an open architecture configuration, such as with Bluetooth® or ZigBee® communication protocols. The telecommunication device 22 can be any portable device, such as a cell phone (which includes a "smartphone"), PDA, laptop computer, Blackberry, another earpiece, or other portable, telemetric device. The portable telecommunication device 22 and the wearable sensor module 21 can telemetrically communicate both to and from each other. Though the main purpose of the portable telecommunication device is to transmit the local wireless signal from the sensor module 21 over longer distances unattainable by the transmitter 14 of the sensor module 21, the telecommunication device 22 can also serve as a method of personal communication and entertainment for the earpiece user.

In some embodiments, the telecommunication device 22 transmits data in only one direction or particular directions. For example, in one embodiment, the portable telecommunication device 22 can receive telemetric information from the sensor module 21 but cannot send out signals to a transmission system 23. The portable telecommunication device 22 may also contain an end-user graphical interface, such as a user interface 24 in the monitoring system 20, such that data from the wearable sensor module 21 can be stored, analyzed, summarized, and displayed on the portable telecommunication device 22. For example, charts relating health and environment, as well as real-time biofeedback and the like, can be displayed on a cell phone, media player, PDA, laptop, or other device. The telecommunication device 22 may also contain physiological and environmental sensors itself, such as sensors for blood pressure, pulse rate, air quality, pulse-oximetry, and the like. Additionally, the telecommunication device 22 can communicate with the wearable sensor module 21 to transfer commands, activate or deactivate sensors, communicate with the user, and the like.

The portable telecommunication device 22 sends/receives wireless information directly to/from a transmission system 23 for transmission to a database (such as personal database 25 and/or anonymous database 26) for storage, analysis, and retrieval of data. The style of transmission system may depend largely on the location of the database. For example, if the database is located in a local computer, the wireless information from the telecommunication device 22 can be sent directly to the local computer. This computer may be connected with the Internet, allowing access to the database from the web. However, the database is more typically located far away from the user and telecommunication module. In this case, the wireless signal from the telecommunication device 22 can be sent to a reception tower and routed through a base station. This information can then be sent to a database through the Internet. A variety of other transmission protocols can be applied for connection between the telecommunication device 22 and the databases 25 and 26.

The personal and anonymous databases 25, 26 represent databases that may or may not be located on the same computer. A difference between these two databases is not the physical location of the database but rather the type of information available on each database. For example, the anonymous database 26, containing aggregated health and environmental data from multiple indistinct monitoring device users, can be public and accessible through the Internet by various users. In contrast, the personal database 25 contains health and environmental data that is personalized for each monitoring device user, including personalized information such as name, birth date, address, and the like. Users can log-in to their personalized information in the personal database 25 through an interactive user interface 24 and compare this information with information from multiple users in the anonymous database 26 via a graphical user interface, etc. In some cases, the wearable sensor module 21 or portable telecommunication device 22 may additionally communicate information not directly related to health and environment, such as physical location, personal information, proximity to various locations or properties, etc., to either database. In some cases, this additional information may be sensed by the wearable sensor module 21 and/or by sensors and/or protocols integrated into portable communication device 22.

The user interface 24 can be a computer monitor, a cell phone monitor, a PDA monitor, a television, a projection monitor, a visual monitor on the wearable sensor module 21, or any method of visual display. (Audible methods and audio-visual methods can also be used for the user interface 24, as well as mechanical methods such as automated brail displays for the blind.) For example, the user may log-in to their personal database 25 through a computer user interface 24 and compare real-time personal health and environmental exposure data with that of other users on the monitoring system 20. In some cases, the data from other users may be anonymous statistics. In some cases, one or more users may have agreements to view the data of one or more other users, and in other cases, users may agree to share mutual personalized data through the Internet.

Figure 3:
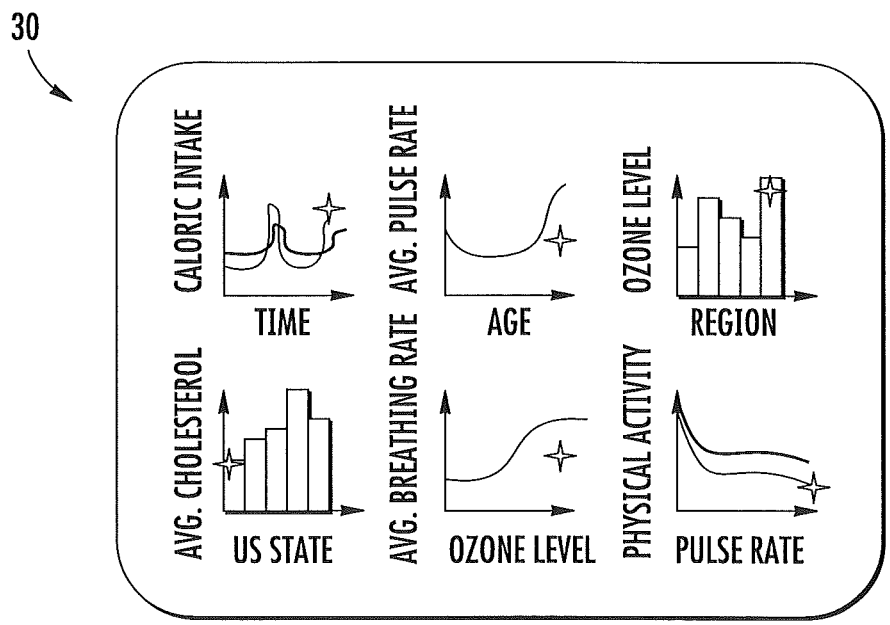
FIG. 3 illustrates a graphical user interface for displaying data, according to some embodiments of the present invention.
Figure 10:
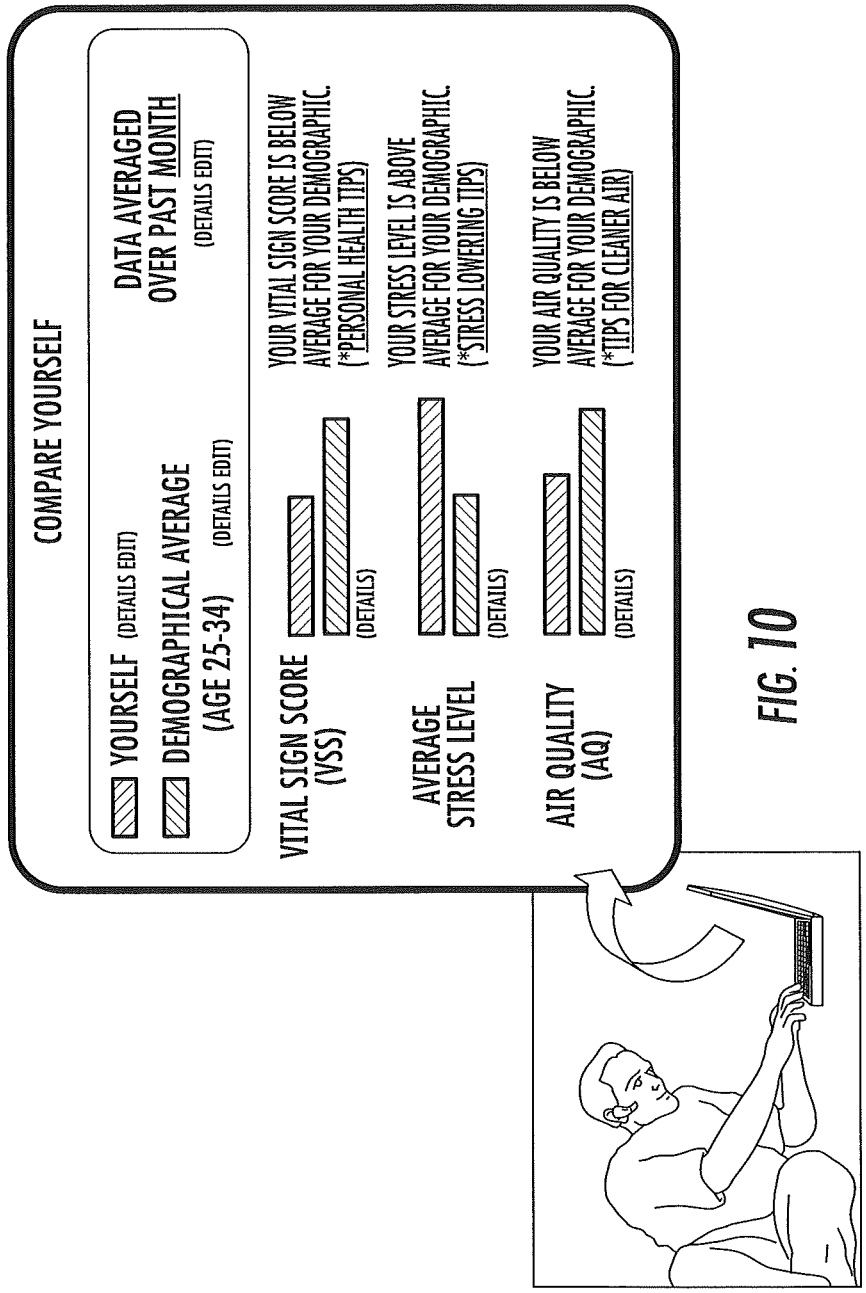
FIG. 10 illustrates the display of demographic comparisons of physiological and environmental information, according to some embodiments of the present invention.

A specific embodiment of a graphical user interface 30 is presented in FIG. 3. FIG. 3 shows an example of how a computer monitor may appear to a user logging-in to their personal database 25 and comparing their own personal data with that of anonymous users in the same monitoring system 20. In this case, data from anonymous users is averaged into certain demographics; the choice of the demographics to be displayed can be selected by the user accessing the personalized database. In the graphical user interface 30 of FIG. 3, the user's personalized data, signified by a star, is compared with statistics from other users in an anonymous database 26. This allows the user to compare his/her health and environment with that of others in selected demographics. FIG. 10 illustrates an exemplary user interface that a user can access to compare himself/herself to others, according to some embodiments of the present invention.

Monitoring system 20 serves not only as a source of useful information from a medical standpoint, but also as a form of entertainment for curious users. It is important to note that health and environmental information from multiple subjects may be updated regularly. In some cases, the regular updates are real-time (or "near-real-time") updates. Thus, information is always new and fresh with respect to daily changes in a group of subjects, and the plots of FIG. 3 are dynamic, changing in time with changing user health and/or environmental information.

The monitoring system 20 can be used in medicine for a variety of important functions. As one example, a doctor can monitor the health of patients through each patient's personalized database 25. If the wearable sensor module 21 contains a dosimeter, the doctor can even monitor the efficacy of prescribed medications, and the physiological response to medications, over time. This dosimetry approach is directly applicable to clinical studies of various treatments. For example, during a clinical trial, the wearable sensor module 21 can collect environmental data, drug dosimetry data, and physiological data from the earpiece user such that researchers can understand the epidemiology between drugs, genes, physiology, environment, and personal health.

Because of the high compliance of the wearable monitoring device 10, primarily due to the dual-modality as a health/environmental monitor and a personal communication/entertainment device, users are prone to wear this device throughout clinical trials, providing more valuable information for drug discovery and the pharmaceuticals market.

As a further example, the health and environmental monitoring system 20 can be used by dieticians to track the caloric intake, health, and physical activity of dieters. Similarly, the monitoring system 20 can be used by athletic trainers to monitor the diet, physical activity, health, and environment of athletes. In many cases professionals are not necessary, and the user can monitor his/her own diet, activity, athletic performance, etc. through the monitoring system without professionals, parents, guardians, or friends monitoring their personal statistics.

In a specific example of the monitoring system 20, a test subject in a clinical trial for a new treatment, such as a new drug, physical therapy, medical device, or the like, is wearing at least one monitor 21. The subject's health and environment are monitored in real-time, and this data is stored on the wearable sensor module 21, the portable telecommunication device 22, the personal database 25, and/or the anonymous database 26. By accessing the stored data, researchers managing the clinical trial can then compare the statistics from multiple users to make correlations between user environment, health, and the effectiveness of treatment.

According to some embodiments of the present invention, a method of monitoring one or more subjects includes collecting physiological and/or environmental information from a monitoring device associated with each respective subject, storing the collected physiological and/or environmental information at a remote storage device, and comparing the stored physiological and/or environmental information with benchmark physiological and/or environmental information to identify at least one behavioral response of the one or more subjects. As described above, each monitoring device includes at least one physiological sensor and/or environmental sensor. Exemplary behavioral responses include behavioral responses to a product and/or service, behavioral responses to product and/or service marketing, behavioral responses to medical treatment, and behavioral responses to a drug.

It should be noted that algorithms for processing personal health and environmental data, diagnosing medical conditions, assessing health states, and the like do not need to be limited to the illustrated monitoring system 20. Various algorithms can also be integrated into the wearable sensor module 21 or telecommunication device 22 according to embodiments of the present invention. A data storage component in at least one of these units allows processed signal data to be stored, analyzed, and manipulated to provide new knowledge to the user. This storage component can be any solid-state storage device, such as flash memory, random-access memory (RAM), magnetic storage, or the like. For example, the wearable sensor module 21 can be programmed to monitor certain habits, such as nail-biting. In this non-limiting example, the physiological sensors 11 may monitor internal sounds, and an algorithm can be implemented to monitor signatures of nail-biting sounds in real-time. If the habit is identified by the algorithm, the communication module 17 may instantly warn the user that the habit is occurring. Alternatively, the algorithm may count the number of times a day the habit occurred, monitor physiological and psychological stress indicators during each occurrence, log each time when the habit occurred, and store environmental data associated with the habit. This stored data can be accessed at a later time, allowing the user to determine what environmental factors cause the physiological or psychological stress associated with nail-biting. As this example shows, these algorithms can take advantage of both physiological sensor data and environmental sensor data.

Figure 11:
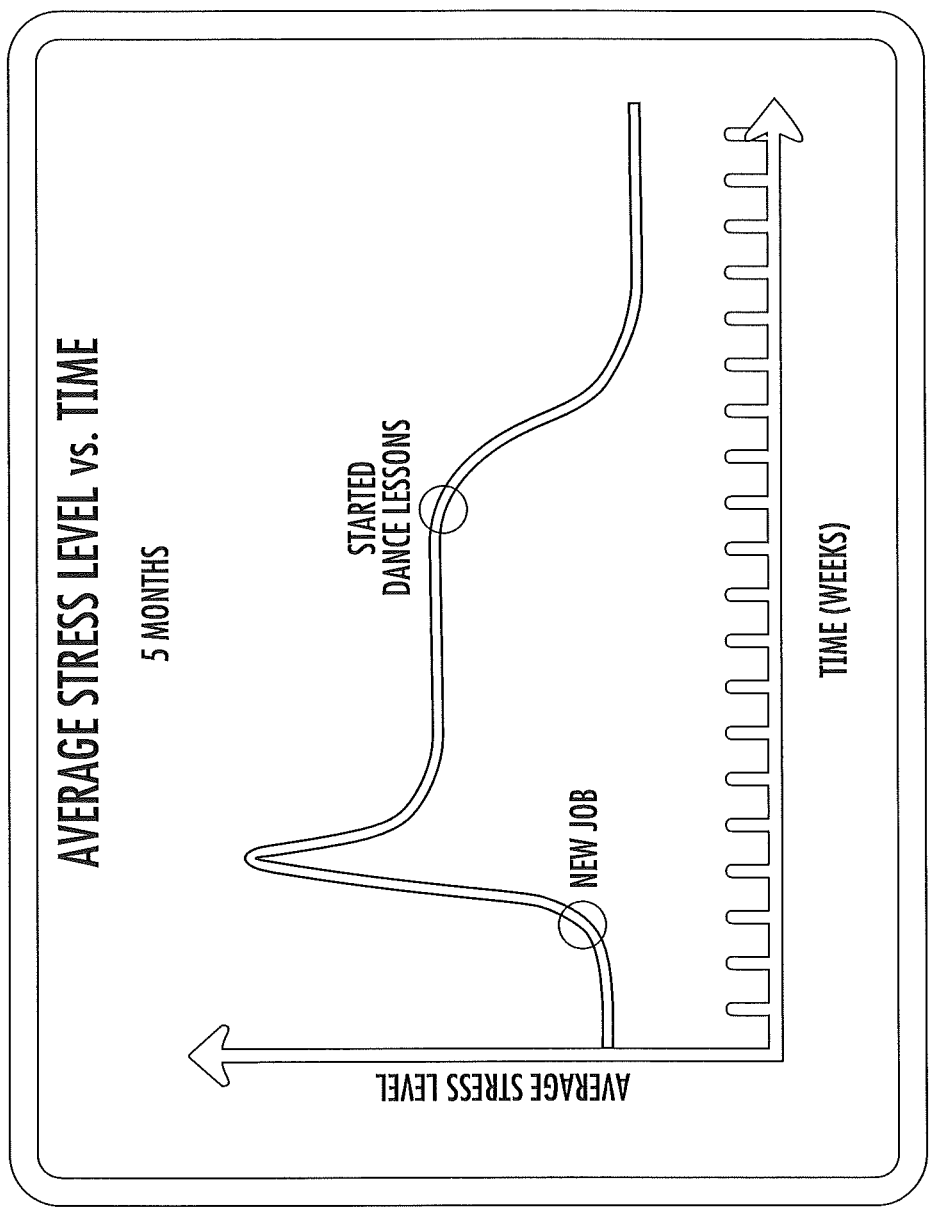
FIG. 11 illustrates the display of stress level over time as measured by a monitoring device, according to some embodiments of the present invention.

According to some embodiments of the present invention, a method of supporting interpersonal relationships includes collecting physiological and/or environmental information from a monitoring device associated with a person when the person is in the presence of another person, determining a stress level of the person using the collected physiological and/or environmental information, and displaying the stress level to the person (or to others). As described above, the monitoring device 10 includes at least one physiological sensor and/or environmental sensor, wherein each physiological sensor is configured to detect and/or measure physiological information from the person, and wherein each environmental sensor is configured to detect and/or measure environmental conditions in a vicinity of the person. The collected physiological and/or environmental information includes indicators associated with stress experienced by the person;

According to some embodiments of the present invention, physiological and/or environmental information collected from the person over a period of time can be stored and subsequently analyzed. For example, a stress level of the person over a period of time can be determined using the stored information, and can be displayed to the person (or to other persons). FIG. 11 illustrates the display of stress over time for a user, according to some embodiments of the present invention.

According to some embodiments of the present invention, physiological and/or environmental information collected from a person can be analyzed to identify a source of stress to the person, and one or more solutions for reducing stress can be recommended to the first person, for example via the monitoring device 10 (or in other ways).

A data storage component may include various algorithms, without limitation. In some embodiments, at least one algorithm is configured to focus processing resources on the extraction of physiological and/or environmental information from the various environmental and/or physiological sensors. Algorithms may be modified and/or uploaded wirelessly via a transmitter (e.g., receiver/transmitter 14 of the wearable monitoring device 10)

The biofeedback functionality of the telemetric wearable monitoring device 10 can be applied towards various gaming applications. For example, one or more subjects can connect their wearable monitoring devices 10 to one or more gaming devices wirelessly through the open architecture network provided by Bluetooth® communication protocol, ZigBee® communication protocol, or other such networks. This allows personal health and environmental information to be transferred wirelessly between the wearable monitoring device 10 and a gaming device. As subjects play a game, various personal health and environmental feedback can be an active component of the game. In a non-limiting embodiment, two users playing a dancing game, such as Dance Dance Revolution, can monitor their vital signs while competing in a dancing competition. In some cases, users having healthier vital signs, showing improved athletic performance, will get extra points ("Vital Points"). In another specific example, this personal health and environmental information can be sent telemetrically to a gaming device to make entertaining predictions about one or more users. Namely, the gaming device may predict someone's life expectancy, love-life, future occupation, capacity for wealth, and the like. These predictions can be true predictions, purely entertaining predictions, or a mixture of both. Sensors measuring external stressors (such as outside noise, lighting conditions, ozone levels, etc.) and sensors measuring internal stresses (such as muscle tension, breathing rate, pulse rate, etc.) integrated into the wearable monitoring device 10 can be used to facilitate predictions by the gaming device. For example, the information from the sensors can be recorded from one or more subjects wearing a sensor module 21 during a series of questions or tasks, and the information can be sent telemetrically to a gaming device. An algorithm processed in the gaming device can then generate an entertaining assessment from the information. This game can be in the form of a video game, with a graphical user interface 24, or it can be a game "in person" through an entertainer. Other games can involve competitions between multiple wearable monitor users for health-related purposes, such as online dieting competitions, fitness competitions, activity competitions, or the like. Combining the telemetric wearable monitoring device 10 with gaming, according to embodiments of the present invention, provides seamless interaction between health and environmental monitoring and the game, through a comfortable telemetric module. Other sensor modules 21 located at various parts of the body can also be used.

An additional non-limiting embodiment of the biofeedback functionality of a wearable sensor module 21, according to some embodiments of the present invention, include monitoring psychological and physiological stress (such as monitoring stress indicators) during a poker game. These stress indicators can be breathing rate, muscle tension, neurological activity, brain wave intensity and activity, core body temperature, pulse rate, blood pressure, galvanometric response, and the like. Users may, for example, use the wearable sensor module 21 to record or display their psychological and physiological stress during a poker game in real-time. This information can be stored or displayed on a portable telecommunication device 22 or sent wirelessly to other parts of the monitoring system 20. The user can use this biofeedback to adjust their psychological and physiological stress (or stress indicators) through force of will. This biofeedback process allows earpiece users to self-train themselves to project a certain "poker face," such as a stoic cold look, a calm cool look, or another preferred look. Additionally, external stressors, such as light intensity and color, external sounds, and ambient temperature, can be sensed, digitized, and transmitted by the wearable monitoring device 10 to a telecommunication device (for storage), providing the user with important information about how the external environment may be affecting their stress response and, hence, poker game. In some games, the stress indicators may be displayed for outside viewers (who are not part of the poker game) as a form of entertainment when watching a group of poker players (each having earpiece modules 21) in a casino, television, or through the Internet.

Physiological and/or environmental information collected from sensors 11, 12 in a wearable module 21 (10) may be corrupted by the motion artifacts of a subject. As a specific example, when measuring pulse rate in a subject via photoplethysmography while the subject is walking, optical scatter associated with footstep-related skin vibrations may be misinterpreted as coming from a pulse. This problem can be especially difficult where footstep rates are on the order of normal human pulse rates. By measuring body motion in real-time via one or more accelerometers inside the wearable monitor 21 (10), sampled pulse rate data can be processed to subtract, reduce, or eliminate signals associated with footsteps. In some cases, the processor 13 may simply send a command to ignore the sampling and/or logging of pulse rate when body motion is detected. In this way, average pulse rate estimate is not convoluted with footstep information. In other cases, the processor 13 may correct for body motion in real time through dynamic feedback from the aforementioned accelerometer. A variety of other body motion sensors, such as acoustic sensors for monitoring footstep sounds and MEMS motion sensors, can also be used to monitor footsteps and correct physiological and/or environmental data for motion artifacts. An important innovation afforded by the databases 25, 26 is that motion artifacts in the data can be corrected by applying algorithms for reviewing the physiological and/or environmental history of each subject, identifying corruptions associated with motion artifacts, and extracting physiological and/or environmental information from corrupted data.

Information collected from one or more subjects wearing a sensor module 21 in the monitoring system 20, can be integrated into a game for a novel gaming experience. For example, information collected from health and environmental monitors worn by a user throughout the day can be used to build a gaming character based on that user. With a group of subjects wearing such monitors throughout the day, a novel gaming environment based on a plurality of real life characters can be generated. Because information from each subject is updated on a regular basis with the monitoring system 20, information about characters can always be fresh and dynamic, changing as the health and environment of each subject changes. Information from a group of subjects sharing a common quality can be summarized into a single character or group of characters based on the aggregated dynamic changes in the health and/or environment within the representative group.

The biofeedback approach is also directly relevant to personal education as a learning tool. For example, monitoring the physiological and psychological response to learning can be used to help users understand if they are learning efficiently. For example, in the course of reading, the wearable sensor module 21 can monitor alertness through galvanometric, brainwave, or vital sign monitoring. The user can then use this information to understand what reading methods or materials are stimulating and which are not stimulating to the earpiece user.

Biofeedback methods, according to embodiments of the present invention can be used as self-training tools for improving performance in public speaking, athletic activity, teaching, and other personal and job-related activities.

A health and environmental monitoring system 20, according to some embodiments of the present invention, enables a variety of additional business methods for exploiting user information collected by the system 20. For example, users can be charged a fee for downloading or viewing data from the personal and/or anonymous databases 25, 26. Alternatively, users may be allowed free access but may be required to register online, providing personal information with no restrictions on use, for the right to view information from the databases. In turn, this personal information can be traded or sold by the database owner(s). This information can provide valuable marketing information for various companies and government interests. The health and environmental data from the databases 25, 26 can be of great value itself, and this data can be traded or sold to others, such as marketing groups, manufacturers, service providers, government organizations, and the like. A web page or web pages associated with a personal and anonymous database 25, 26 may be subject to targeted advertising. For example, if a user shows a pattern of high blood pressure on a personal database 25, a company may target blood pressure treatment advertisements on the user interface 24 (i.e., web page) while the user is logged-in to the personal database through the user interface 24. For example, because various health and environmental statistics of subjects in the monitoring system 20 will be available on the database, this information can be used to provide a targeted advertising platform for various manufacturers. In this case, a database manager can sell information to others for targeted advertising linked to a user's personal statistics. In some cases, a database owner does not need to sell the statistics in order to sell the targeted advertising medium. As a specific example, a company can provide a database owner with statistics of interest for targeted advertising. For example, the company may request advertising a weight-loss drug to anonymous users having a poor diet, high caloric intake, and/or increasing weight. A database manager can then charge the company a fee for distributing these advertisements to the targeted users as they are logged-in to the database website(s). In this way, the users remain anonymous to the company. Because targeted advertisements can be such a lucrative market, income from these sources may eliminate the need for charging users a fee for logging-in to the databases 25, 26.

According to some embodiments of the present invention, a method of delivering targeted advertising to a person includes collecting physiological and/or environmental information from the person, selecting an advertisement for delivery to the person based upon the collected physiological and/or environmental information, and delivering the selected advertisement to the person. Collecting information includes receiving physiological and/or environmental information from a monitoring device associated with the person. Selecting an advertisement includes analyzing the received physiological and/or environmental information to identify a physiological condition of the person and/or environmental condition in a vicinity of the person, and selecting an advertisement for a product or service related to an identified physiological and/or environmental condition. Delivery of a selected advertisement can be via any of many different channels including, but not limited to, email, postal mail, television, radio, newspaper, magazine, the internet, and outdoor advertising.

There are many ways to profit from a health and environmental monitoring system 20, according to embodiments of the present invention. For example, information from subjects can be used to target online advertisements or links to a particular subject or group of subjects, where these advertisements or links are tailored to information collected from each subject in the monitoring system 20 through sensor modules 21. In some cases, a targeted online link, tailored to a subject or group of subjects, may not necessarily constitute an advertisement but rather a targeted link corresponding to a targeted good or service. Additionally, advertisements need not be limited to online advertisements. The collected information can be used for targeted mailings, television commercials, newspaper/magazine ads, billboards, and the like.

A wearable sensor module 21 and health and environmental monitoring system 20 can enable a variety of research techniques. For example, a plurality of monitoring devices 10 worn by users can be used in marketing research to study the physiological and psychological response of test subjects to various marketing techniques. This technique solves a major problem in marketing research: deciphering objective responses in the midst of human subjectivity. This is because the physiological and psychological response of the earpiece user largely represents objective, unfiltered information. For example, users that are entertained by a pilot TV program would have difficulty hiding innate vital signs in response to the program. The data generated by the wearable sensor module 21 during market research can be transmitted through any component of the telemetric monitoring system 20 and used by marketing researchers to improve a product, service, or method.

Another method provided by the monitoring system 20 is to charge users of the monitoring system for usage and service (such as compilation service). For example, a clinical trial company may pay a fee for accessing the databases 25, 26 of their test subjects during medical research. In this case, these companies may buy modules 21 and pay for the service, or the modules 21 may be provided free to these companies, as the database service fee can provide a suitable income itself. Similarly, doctors may pay for this service to monitor patients; fire fighters and first responders may pay for this service to monitor personnel in hazardous environments; and athletic trainers may pay for this service to monitor athletes. Also, users can pay for the database service directly themselves. Because these databases 25, 26 are dynamic, updated regularly via a wearable sensor module 21 of each user, with data changing with time for individual users and users en mass, these databases can maintain a long-term value. In other words, there may always be new information on the databases 25, 26.

Another embodiment of the present invention involves methods of combining information from various sensors 11, 12 into a meaningful real-time personal health and environmental exposure assessment in a recording device. The meaningful assessment is generated by algorithms that can be executed in the sensor module 21, in the portable telecommunication device 22, or through various other electronic devices and media within the monitoring system 20. In one embodiment, raw or preprocessed data from the sensor module 21 is transmitted wirelessly to the telecommunication device 22, and this device executes various algorithms to convert the raw sensor data (from one or more sensors) into a meaningful assessment for the user. For example, a blood pressure assessment may be processed from stored raw data on personal database 25 and/or anonymous database 26 collected from pulse rate sensors, pulse volume sensors, and blood flow sensors in the wearable sensor module 21. In another embodiment these algorithms are executed within the sensor module 21 itself, without the need for processing in the telecommunication device 22, through a processor 13 inside the module 21 (10). The output from these algorithms can be viewed as charts, graphs, figures, photos, or other formats for the user to view and analyze. Preferably, these formats display various health factors over time with respect to a particular environment, with health factor intensity on the dependent axis and time or environmental factor intensity on the independent axis. However, virtually any relationship between the physiological data and environmental data can be processed by an algorithm, and these relationships can be quantitative, qualitative, or a combination of both.

One innovation involves applying the wearable sensor module 21 towards a physical or mental health assessment method. An algorithm may combine data from health and environmental sensors 11, 12 towards generating a personal overall health assessment for the user, conditional to a particular environment. For example breathing rate, pulse rate, and core body temperature can be compared with ozone density in the air for generating an ozone-dependent personal health assessment. In another specific example of this innovation, information from the sensors 11, 12 can be used to monitor overall "mood" of a user in a particular environment. More particularly, algorithmic processing and analyzing of data from sensors for core body temperature, heart rate, physical activity, and lighting condition can provide a personal assessment of overall mood conditional on external lighting conditions.

Mood sensing in the wireless sensing monitoring system 20 can be implemented in a variety of novel ways. A case example is that of a girl wearing a sensor module 21, in the form factor of a Bluetooth® headset (earpiece), embedded with sensors and a processor for monitoring overall mood. As the girl's mood changes, the headset monitor 21 senses, processes, and transmits mood to portable communication device, such as a cell phone. The cell phone may then send a text message (or other type of communication), manually or automatically via a stored program, to a boyfriend, notifying the boyfriend of a change in mood. This allows the boyfriend to respond more rapidly and efficiently to mood changes. Similarly, aggregated mood data from a variety of users wearing similar or identical monitors can be used to track mood in a population study for one or more groups of people.

An application of the health and environmental monitoring system 20 is supporting interpersonal relationships between individuals and/or groups of individuals. For example, subjects wearing a monitoring device 21 (10) can track stress rates when interacting with certain other subjects. As a more specific example, a subject wearing a monitoring device 21, containing physiological and/or environmental sensors for tracking indicators associated with stress, can track their stress level in the presence of their spouse, children, coworkers, etc. through the user interface 24. As the subject interacts throughout the day, the wearable monitoring device 21 may communicate stress updates through the wireless monitoring system 20 for storage in databases 25 and/or 26. Through the view screen of a computer, the user can then track a history of stress levels while interacting with certain individuals. The correlation between stress level and particular individuals may be decided based on the time of day or a time mark selected by the subject wearing the monitor 21. In some cases, the monitor 21 may be programmed to recognize other individuals audibly and/or visually or through a certain environment common to other individuals through sensors 11, 12 integrated into the monitor 21 (10), and this correlation may then be transmitted wirelessly to the databases 25 and/or 26 for tracking stress with respect to a particular interpersonal relationship. The stress record stored in the databases can then be used by professionals or the individuals themselves to uncover the sources of stress and recommend solutions or therapies for reducing stress in an interpersonal relationship. In some cases, the correlation with the stress of a subject and the subject's environment may be all that is of interest, in which case detecting other individuals is not necessary.

Applying sensor information from the sensor monitoring system 20 towards predictions for individual subjects and groups of subjects is another embodiment of the present invention. Health and/or environmental information from individuals in the monitoring system can be used to predict an individual's behavior, health, the onset of a health condition, etc. Collectively, information from multiple subjects in the monitoring system 20 can be used to predict the outbreak of a disease, environmental situation, traffic conditions, mass behavior (such as market behavior), and the like. As a specific examples, sensors for monitoring physiological and/or environmental parameters associated with influenza may monitor changes in core body temperature, voice pitch changes, pulse rate changes, etc. in a subject, or group of subjects, wearing a module 21, and this information may be processed into a prediction of the onset of influenza for the subject or group of subjects. Indeed, the onset of a mass outbreak can be predicted. A variety of predictive techniques can be used to predict behavior based on user information from the monitoring system 20. Predictions can be made by processing data stored in the databases 25, 26 with predictive algorithms, such as neural network-based programs and other computer programs. In some cases, predictions can be made simply by processing trends through human analysis, computer analysis, or a combination of both. In some cases, predictions may be processed by the internal processor 13 inside the wearable health module 21 (10).

Information from the health and environmental monitoring system 20 can be used to track, direct, and predict the marketing, advertising, distribution, and sales of goods or services tailored towards one or more subjects or groups in the monitoring system. As an example, trends in high stress for a subject wearing a monitor 21 can be processed into information relating the specific stress-related product needs, such as medications, spas, or therapies, tailored for that specific subject. Similarly, trends in poor health may communicate corrective action to the user, through the aforementioned wireless protocol, or through medical professionals to the user. In some cases, warnings may be communicated to first responders to assist a subject. Information from groups of individuals in the monitoring system 20 may be used to track, direct, and predict the marketing, advertising, distribution, and sales of goods or services tailored towards a group or region.

Although many examples herein relate to generating profiles for individuals or groups wearing monitors 21 in a monitoring system 20, it should be understood that embodiments of the present invention have broad applicability to users not wearing monitors 21. Profiles can be generated for individuals not wearing monitors 21 based on similarities with one or more others who do wear monitors 21. Namely, individuals may be targeted for advertisements, marketing, distribution, and sales for goods and services based on a relationship with subjects wearing monitors 21. For example, individuals matching the demographics of a subject or group of subjects being monitored in the monitoring system 20 may received targeted ads, links, marketing, goods/services, and the like. Additionally, users viewing information from the anonymous database 26 may be subject to targeted or untargeted marketing and sales aspects, regardless of whether or not they wear a module 21.

The monitoring system 20 does not require subjects to wear monitors 21 continuously to be functional. Subjects wearing modules 21 for merely a few minutes a day can provide useful information for the monitoring system 20 and for the individuals themselves.

An earpiece/headset form factor for a wearable sensor module 21 can be utilized for monitoring or predicting traffic-related conditions for automobiles and other vehicles. As a specific example, a wearable earpiece module 21, containing physiological and environmental sensors, can provide information about the stress of a subject while driving, as well as the speed of the subject, environmental conditions surrounding the subject, alertness of the subject, and the like. This can be accomplished by monitoring heart rate, breathing rate, core body temperature, acceleration, the weather conditions, air quality, and the like with sensors 11, 12. Information from multiple subjects can be used to track and study the stress of a group of individuals with certain traffic-related conditions. Additionally, predictions about traffic jams, road accidents, traffic flow can be estimated based on processed information stored in the remote databases 25, 26. This information can also be used to assist infrastructure decisions that will reduce the stress of drivers, improve traffic flow, and prevent automotive accidents. In some cases, this information may be used in studies to understand the interaction between stress, road conditions, environment, and the like.

Figure 12:
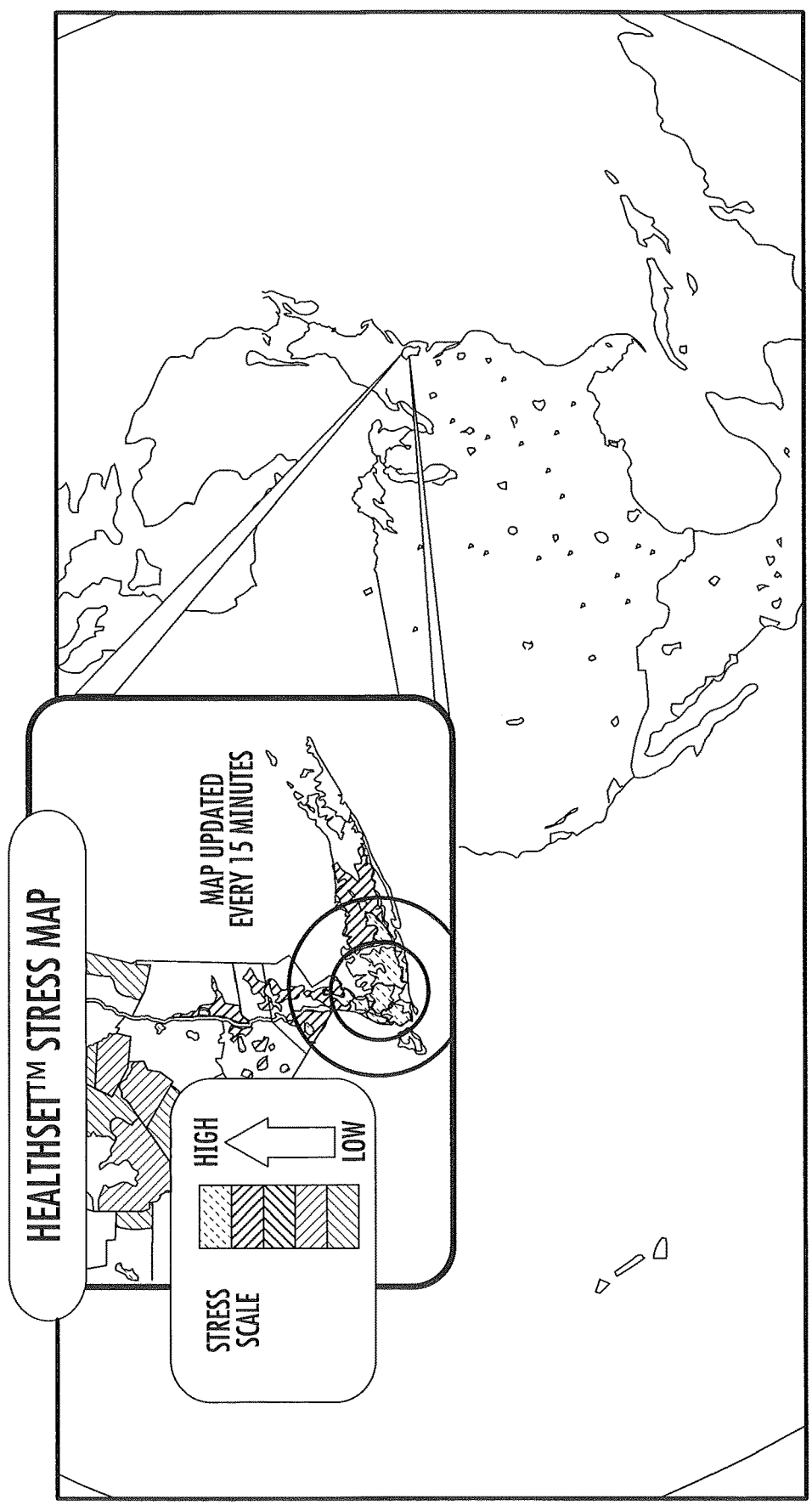
FIG. 12 illustrates the display of a healthy/stress map, according to some embodiments of the present invention.

In some embodiments, information from sensors in a sensor monitoring system 20 can be used to generate real-time maps related to physiological and/or environmental conditions of groups of subjects over a geographical landscape. For example, a real-time health/stress map (see, for example, FIG. 12) or real-time air quality map can be generated through a user interface 24 for informational or entertainment value to one or more viewers. Aggregated data stored in the anonymous database 26 can be processed into a map by correlating the location of each subject with physiological and environmental data measured by sensors 11, 12 integrated into a wearable monitor 21 worn by the each subject. Location information can be provided through the existing cellular infrastructure, through the triangulation of wireless signals related to each subject, or through location sensors integrated into the monitor 21 or portable telecommunication device 22 (such as GPS sensors), or the like. These maps can be dynamic and real-time based on wireless updates from each subject. These maps can be local, regional, state-wide, national, world-wide, and the like.

Earpiece monitoring devices described herein need not be embodied within headsets only. For example, an wearable earpiece module 10 according to embodiments of the present invention can be a hearing aid, an earplug, an entertaining speaker, the earpiece for an IPOD®, Walkman®, or other entertainment unit, a commercial headset for a phone operator, an earring, a gaming interface, or the like. A wearable earpiece module 10 covers the broad realm of earpieces, ear jewelry, and ear apparatuses used by persons for entertainment, hearing, or other purposes both inside and outside of health and environmental monitoring.

Moreover, two earpiece modules 10 may be utilized, according to some embodiments of the present invention; one for each ear of a person. In some cases, dual-ear analysis can be performed with a single headset having dual earpieces. Dual-ear analysis with two earpiece modules can be used, for example, to compare the core temperature of each tympanic membrane in order to gauge brain activity comparing each brain hemisphere. In another case, acoustical energy, including ultrasonic energy, can be passed from one earpiece module to the other, with acoustic absorption and reflection being used to gauge various physiological states. For example, this technique can be used to gauge hydration level in the head or brain by estimating the acoustical energy absorption rate and sound velocity through the head of the user.

Figure 4:
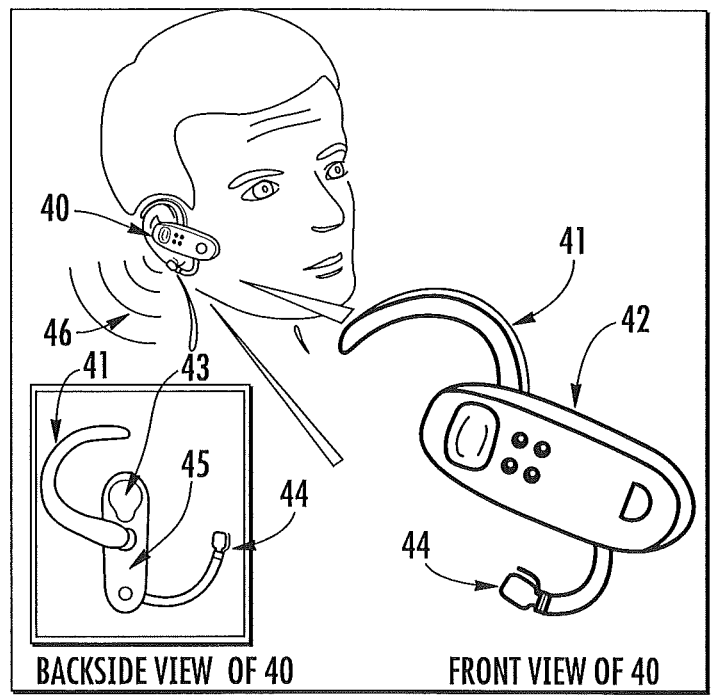
FIG. 4 illustrates an earpiece module according to some embodiments of the present invention.

A variety of form factors for wearable monitoring devices 10 may be used in the present invention. The form-factor of a wrist-watch, belt, article of clothing, necklace, ring, body piercing, bandage, electrode, headband, glasses or sunglasses, cast (i.e., for broken bones), tooth filling, etc. are but a few examples. A variety of earpiece styles, shapes, and architectures can be used for the case of where a wearable monitoring device 10 is an earpiece module, according to embodiments of the present invention. A non-limiting embodiment of an earpiece module is illustrated in FIG. 4. The illustrated earpiece 40 fits over the ear of a person and is held in place by an ear support 41 (also called the "earpiece attachment component" 15). The illustrated earpiece module 40 also includes an earpiece body 42, an earpiece fitting 43, and an optional earlobe clip 44. The earpiece may also contain an adjustable mouthpiece 52 (FIG. 5B) and/or a pinna cover 53 (FIGS. 5A-5B) described below. The earpiece 40 connects with the ear canal of a person through an earpiece fitting 43 located on the backside 45 of the earpiece 40. The earpiece fitting 43 transmits sound to the inner ear and eardrum. Health and environmental sensors are integrated primarily within or along the earpiece body 42, including the earpiece backside 45. However, an earlobe clip 44 can contain various health and environmental sensors as well. In some cases, health and environmental sensors can be integrated within or along the ear support 41, the adjustable mouthpiece 52, the earpiece fitting 43, or the pinna cover 53. Raw or processed data 46 from these sensors can be wirelessly transferred to a recording device or a portable telecommunication device 22 (FIG. 2). In some embodiments of the present invention, a recording device can be located within or about the earpiece 40 itself. In some cases, this recording device is flash memory or other digitized memory storage. The types of health and environmental factors which may be monitored have been previously described above for the wearable monitoring device 10.

It should be understood that the earpiece body 42 can be any shape and size suitable for wear around or near the ear. In some cases, the earpiece body and earpiece fitting can be one and the same structure, such that the earpiece body-fitting is a small fitting inside the ear. In many cases, it is desirable to seal off or partially seal off the ear canal so as to prevent sounds from entering or leaving the ear such that auscultatory signal can more easily be extracted from the ear canal through devices (such as microphones) in the earpiece body-fitting.

It should be noted that the invention is not limited to the exemplary earpiece 40 of FIG. 4. Other earpiece configurations are also capable of integrating health and environmental sensors for portable, noninvasive, real-time health monitoring according to embodiments of the present invention. For example, the earlobe clip can be modified to reach other surfaces along or near a person's ear, head, neck, or face to accommodate electrical or optical sensing. Similarly, more than one clip may be integrated into the earpiece. Sensors can be integrated into the earpiece-fitting. In such embodiments, the sensors may be integrated into a module in the earpiece-fitting. Environmental sensors are preferably located on the outside of the earpiece through a region on the earpiece frontside. This allows access to air in the vicinity of the earpiece user. However, environmental sensors can be located anywhere along the earpiece module 40.

Figures 5A, 5B:
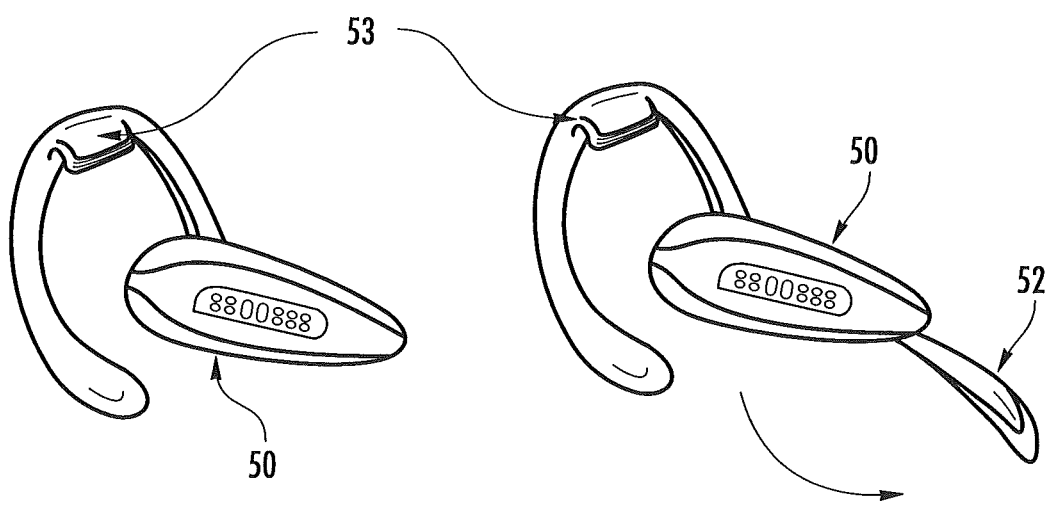

FIGS. 5A-5B illustrate an embodiment of an earpiece module 50 with an adjustable mouthpiece 52 and a pinna cover 53. The earpiece 50 contains a region where an adjustable mouthpiece 52 can be swiveled, extended, pulled, extracted, flipped, or ejected towards the mouth. A microphone at the end of the mouthpiece 52 can be used to improve personal communication through the earpiece 50. Sensors integrated into the mouthpiece 52 can be used to monitor, for example, exhaled breath for respirometry and inhalation/exhalation monitoring. Carbon dioxide, oxygen, nitrogen, water vapor, and other respired gases and vapors can be monitored, providing an overall assessment of health. Additionally, VOCs VOC's and other vapors exhaled by the breath can be monitored for diagnosing various disease states, such as diabetes, obesity, diet, metabolism, cancer, hepatic or renal health, organ functioning, alcoholism, halitosis, drug addiction, lung inflammation, voice analysis, voice distinction, and the like. The mouthpiece 52 is in a retracted or stored position in FIG. 5A and is in an extended or operative position in FIG. 5B.

Figure 6:
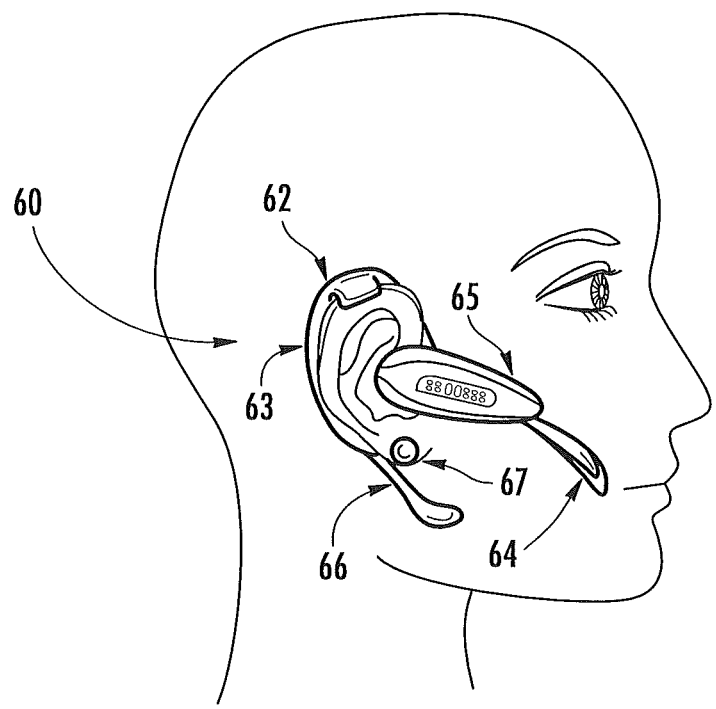
FIG. 6 illustrates an earpiece module incorporating various physiological and environmental sensors, according to some embodiments of the present invention, and being worn by a user.

Another multifunctional earpiece module 60, according to embodiments of the present invention, is illustrated in FIG. 6. The illustrated earpiece module 60 includes the embodiments described with respect to FIGS. 4 and 5A-5B, such as a pinna cover 62, an ear support 63, a mouthpiece 64, an earpiece body 65, and the like. Additionally, the earpiece module 60 may contain an extension 66 with sensors for monitoring jaw motion, arterial blood flow near the neck, or other physiological and environmental factors near the jaw and neck region.

The person illustrated in FIG. 6 is also wearing an earring monitor 67 according to some embodiments of the present invention. Because at least one portion of an earring may penetrate the skin, earring monitor 67 may contain sensors and telemetric circuitry that provide access to various blood analytes through iontophoresis and electrochemical sensing that may not be easily accessible by the other portions of the earpiece module 60. Additionally, the earring 67 may provide a good electrical contact for ECG or skin conductivity.

Figure 7:
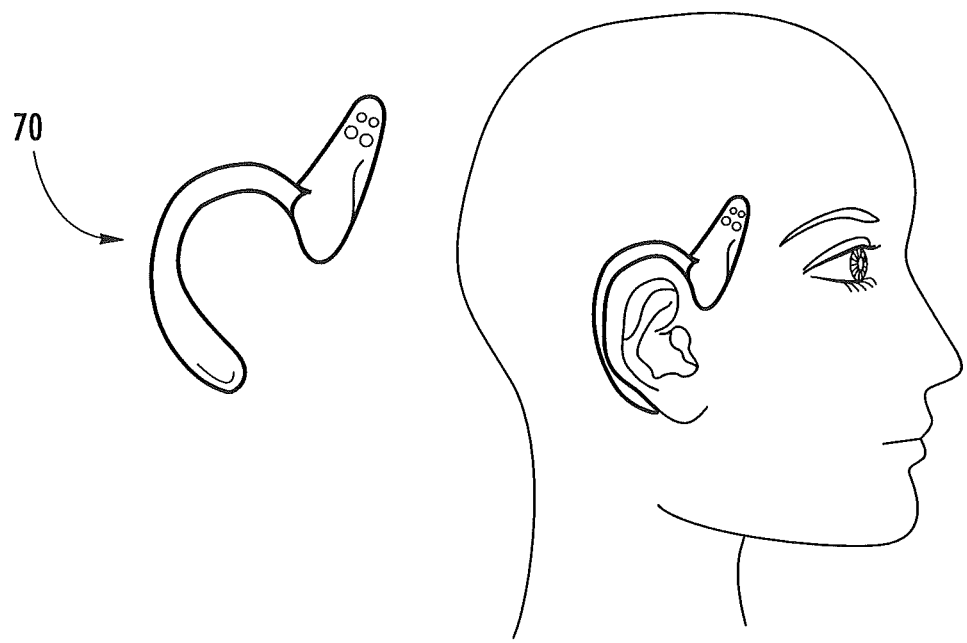
FIG. 7 illustrates an earpiece module according to other embodiments of the present invention that includes a temple module for physiological and environmental monitoring.

Embodiments of the present invention are not limited to earpiece modules. Other types of modules may be utilized that attach to other portions of a person's body. For example, a temple module 70 having a similar design as the earpiece module design 10 can also be employed, as illustrated in FIG. 7. A temple module 70 has the benefit of being close to physiological areas associated with stress, intracranial pressure, brain activity, and migraines. Additionally, a temple module can monitor physiological activity associated with the onset of a stroke, such as increased or decreased blood flow and/or oxygen flow to the brain.

Figure 8:
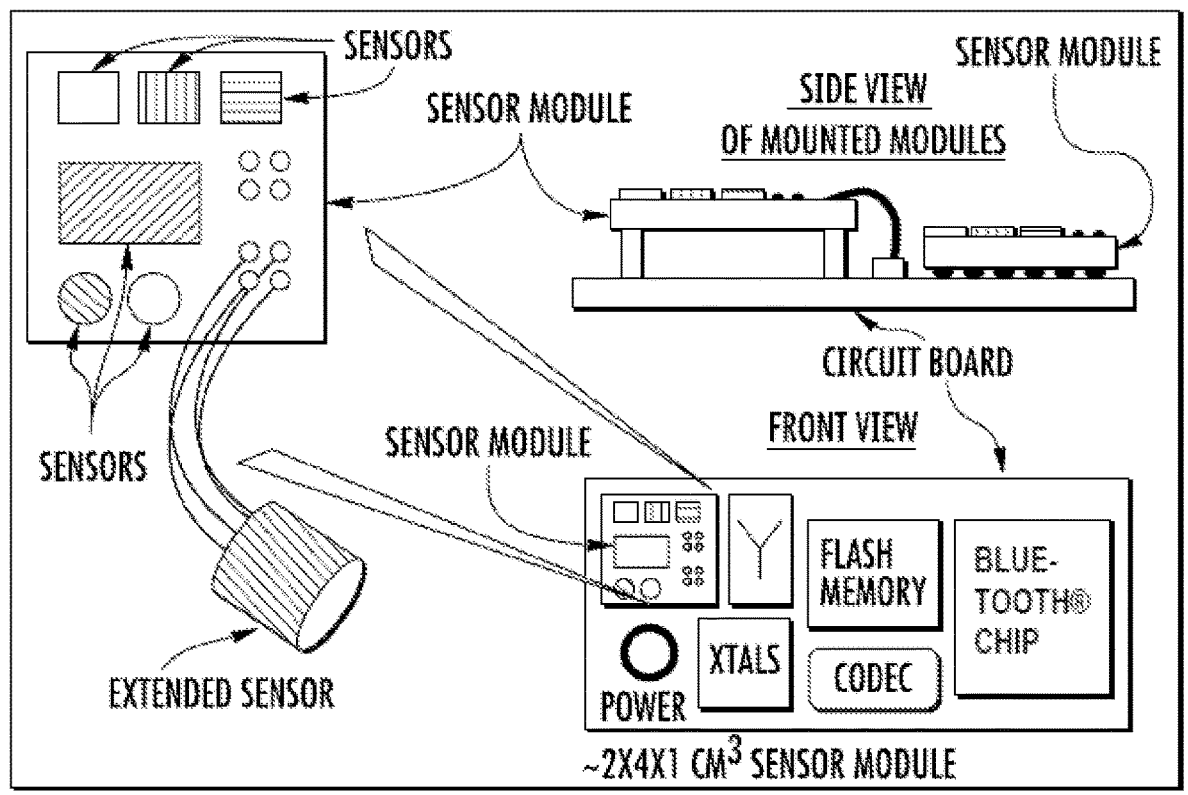
FIG. 8 illustrates a monitoring device having a plurality of health and environmental sensors and mounted onto a Bluetooth® headset module, according to some embodiments of the present invention.

FIG. 8 illustrates a monitoring device 10, according to some embodiments of the present invention, that is integrated into a telemetric Bluetooth® module. Though a Bluetooth® module is illustrated, it should be understood that other telemetric modules can be used. Telemetric modules according to some embodiments of the present invention may operate in open architecture protocols, allowing multiple telemetric devices to communicate with each other. A Bluetooth® module (including the monitoring device) according to some embodiments of the present invention is integrated into a wearable earpiece module (i.e., monitoring device 10 described above). The monitoring device illustrated in FIG. 8 contains one or more sensors, and is mounted onto a Bluetooth® module. In one embodiment, the sensor module is directly soldered onto the Bluetooth® module. In another embodiment, the sensor module is elevated from the Bluetooth® module with spacers, and a cable or electrical wires connect between the sensor module and the Bluetooth® module. The module may be elevated in embodiments where the sensors need to be exposed to the environment. For example, the sensors may need to be exposed through the frontside region of an earpiece module, and the Bluetooth® module may fit too deeply into the earpiece module to provide sensor access to the external environment. In some cases, contact leads or vias may connect between the sensor module and an extended sensor or an additional sensor module. This allows the extended sensor or sensor module to be flexibly mounted anywhere inside, along, outside, or about the wearable sensor module 10. Extended sensors can be especially useful for 4-point galvanometric monitoring of skin conductance, pulse oximetry, and volatile organic compound monitoring.

Pulse oximetry is a standard noninvasive technique of estimating blood gas levels. Pulse oximeters typically employ 2 or more optical wavelengths to estimate the ratio of oxygenated to deoxygenated blood. Similarly, various types of hemoglobin, such as methemoglobin and carboxyhemoglobin can be differentiated by measuring and comparing the optical absorption at key red and near-infrared wavelengths. Additional wavelengths can be incorporated and/or replace conventional wavelengths. For example, by adding additional visible and infrared wavelengths, myoglobin, methemoglobin, carboxyhemoglobin, bilirubin, SpCO2, and blood urea nitrogen (BUN) can be estimated and/or monitored in real-time in addition to the conventional pulse oximetry SpO2 measurement.

Blood hydration can also be monitored optically, as water selectively absorbs optical wavelengths in the mid-IR and blue-UV ranges, whereas water can be more transparent to the blue-green wavelengths. Thus, the same optical emitter/detector configuration used in earpiece pulse oximetry can be employed for hydration monitoring. However, mid-IR or blue optical emitters and detectors may be required. Additionally, monitoring the ratio of blue-green to other transmitted or reflected wavelengths may aid the real-time assessment of blood hydration levels. Blood hydration can also be monitored by measuring changes in capacitance, resistance, or inductance along the ear in response to varying water content in the skin tissues or blood. Similarly, hydration can be estimated by monitoring ions extracted via iontophoresis across the skin. Additionally, measuring the return velocity of reflected sound (including ultrasound) entering the head can be used to gauge hydration. These hydration sensors can be mounted anywhere within or along an earpiece or other monitoring device 10. It should be noted that other hydration sensors can also be incorporated into a module.

A variety of techniques can be used for monitoring blood metabolites via an earpiece module, such as wearable monitoring device 10. For example, glucose can be monitored via iontophoresis at the surface of the skin combined with enzyme detection. Blood urea nitrogen (BUN) can be monitored by monitoring UV fluorescence in blood (through the skin) or by monitoring visible and mid-IR light absorption using the pulse oximetry approach described above. Various ions such as sodium, potassium, magnesium, calcium, iron, copper, nickel, and other metal ions, can be monitored via selective electrodes in an earpiece module following iontophoresis through the skin.

Cardiopulmonary functioning can be evaluated by monitoring blood pressure, pulse, cardiac output, and blood gas levels via earpiece modules, and other monitoring apparatus in accordance with some embodiments of the present invention. Pulse rate and intensity can be monitored through pulse oximetry (described above) as well as by sensing an increase in oxygenated blood with time. Pulse rate and blood flow may also be assessed through impedance measurements via galvanometry near a blood vessel. Additionally, pulse rate and blood flow may be assessed through a fast-response thermal energy sensor, such as a pyroelectric sensor. Because moving blood may temporarily increase or decrease the localized temperature near a blood vessel, a pyroelectric sensor will generate an electrical signal that is proportional to the total blood flow in time.

Blood pressure can be monitored along an earlobe, for example. According to some embodiments of the present invention, a digital blood pressure meter is integrated into an earpiece module, such as earpiece 40 of FIG. 4. A compact clip, containing actuators and sonic and pressure transducers, can be placed along the earlobe, and systolic and diastolic pressure can be measured by monitoring the pressure at which the well-known Korotkoff sound is first heard (systolic), then disappears (diastolic). This technique can also be used to monitor intra-cranial pressure and other internal pressures. Blood pressure may also be measured by comparing the time between pulses at different regions of the body. For example, sensors for monitoring pulse rate and blood volume can be located in front of the ear and behind the ear or at the earlobe, and the time between the detection of each pulse from each sensor, as well as the volume of blood passed, can be processed by a signal processor 13 into an indication of blood pressure.

Electrodes within or about an earpiece can also be utilized to monitor blood gases diffused through the skin, giving an indication of blood gas metabolism. For example, a compact Severinghaus electrode can be incorporated within an earpiece module for the real-time monitoring of CO2 levels in the blood, for example, through an earlobe connector, a sensor region of an earpiece fitting, or along or about an ear support. These Severinghaus-type electrodes can also be used to monitor other blood gases besides CO2, such as oxygen and nitrogen.

Organ function monitoring includes monitoring, for example, the liver, kidneys, pancreas, skin, and other vital or important organs. Liver quality can be monitored noninvasively by monitoring optical absorption and reflection at various optical wavelengths. For example, optical reflection from white LEDs or selected visible-wavelength LEDs can be used to monitor bilirubin levels in the skin and blood, for a real-time assessment of liver health.

Monitoring neurological functioning can be accomplished via electrodes placed at the ear, near the ear, or along another surface of the body. When such electrodes are placed along the forehead, this process is described as electroencephalography, and the resulting data is called an electroencephalogram (EEG). These electrodes can be either integrated into an earpiece module or connected to an earpiece module, according to some embodiments of the present invention. For example, an earlobe clip (e.g., 44, FIG. 4) can be modified to conform with EEG electrodes or other electrodes for measuring brain waves or neurological activity. For monitoring neurological functioning, a temple earpiece (e.g., 70, FIG. 7) may also be used. Electrodes may be positioned in a temple earpiece region near the temples of a user for direct contact with the skin. In some embodiments, direct contact is not necessary, and the neurological functioning can be monitored capacitively, inductively, electromagnetically, or a combination of these approaches. In some embodiments, brain waves may couple with low frequency acoustical sensors integrated into an earpiece module.

A person's body motion and head position can be monitored by integrating a motion sensor into an earpiece module (e.g., 40, FIG. 4) Two such compact motion sensors include gyroscopes and accelerometers, typically mechanical or optical in origin. In some embodiments, an accelerometer may be composed of one or more microelectromechanical systems (MEMS) devices. In some embodiments, an accelerometer can measure acceleration or position in 2 or more axes. When the head is moved, a motion sensor detects the displaced motion from the origin. A head position monitor can be used to sense convulsions or seizures and relay this information wirelessly to a recording device. Similarly, head position monitoring may serve as a feedback mechanism for exercise and athletic training were head positioning with respect to the body is important. Additionally, the head position monitoring can be used to monitor when someone has fallen down or is not moving.

Body temperature, including core and skin temperature, can be monitored in real-time by integrating compact infrared sensors into an earpiece module, according to some embodiments of the present invention. Infrared sensors are generally composed of thermoelectric/pyroelectric materials or semiconductor devices, such as photodiodes or photoconductors. Thermistors, thermocouples, and other temperature-dependent transducers can also be incorporated for monitoring body temperature. These sensors can be very compact and thus can be integrated throughout an earpiece module. In some embodiments, these sensors may be mounted along the backside of an earpiece body, as illustrated in FIG. 4, where the earpiece connects with the ear canal. Temperature sensors aimed at the tympanic membrane may be more accurate than sensors aimed in other directions.

In some embodiments of the present invention, a pedometer can be integrated into an earpiece module to measure the number of steps walked during a day. Pedometers that can be integrated into an earpiece module include, but are not limited to, mechanical pedometers (usually implementing a metallic ball or spring), microelectromechanical systems (MEMS) pedometers, inertial sensor pedometers, accelerometer-based pedometers, accelerometry, gyroscopic pedometers, and the like.

In some embodiments of the present invention, a pedometer for an earpiece module employs an acoustic sensor for monitoring the characteristic sounds of footsteps channeled along the ear canal. For example, an acoustic sensor can be integrated into an earpiece housing (e.g., 42, FIG. 4) along the backside thereof (e.g., 45, FIG. 4) and/or within an earpiece fitting thereof. The sounds generated from footsteps can be detected and analyzed with a signal processor using a noise cancellation or signal extraction approach to identify footstep sounds in the midst of convoluting physiological noise. In this embodiment, digitized electrical signals from footstep sounds from outside the body are compared with digitized electrical signals from footstep sounds traveling through the body (and ear canal), and only the spectral features associated with both types of digitized signals are amplified. This provides a new signal that contains cleaner information about footsteps.

Breathing characteristics can be monitored in a manner similar to that of acoustic pedometry (described above) via auscultatory signal extraction. In some embodiments, an acoustic sensor in an earpiece module is used to sense sounds associated with breathing. Signal processing algorithms are then used to extract breathing sounds from other sounds and noise. This information is processed into a breathing monitor, capable of monitoring, for example, the intensity, volume, and speed of breathing. Another method of monitoring breathing is to employ pressure transducers into an earpiece module. Changes in pressure inside or near the ear associated with breathing can be measured directly and, through signal processing, translated into a breathing monitor. Similarly, optical reflection sensors can be used to monitor pressure in or near the ear by monitoring physical changes in the skin or tissues in response to breathing. For monitoring the physical changes of the tympanic membrane in response to breathing, and hence ascertaining breathing rate, an optical signal extraction approach may be employed. At least one color sensor, or colorimetric sensor, can be employed to monitor changes in color associated with breathing and other health factors.

It should be noted that some embodiments of the present invention incorporate health sensors that do not employ chemical or biological reagents for monitoring various health factors. This is because such sensors have traditionally required larger instrumentation (not suitable for portability) and/or disposable samplers (not acceptable to most end users). However, sensors employing chemical or biological reagents may be incorporated into earpiece modules, according to some embodiments of the present invention. For example, the diffusion of analyte through the skin can be monitored electrically or optically by selective binding to enzymes or antibodies contained in the health sensors integrated into an earpiece module. In some cases, iontophoresis, agitation, heat, or osmosis may be required to pull ions from the skin or blood into the sensor region for monitoring health factors. In some cases, these analytes may be tagged with markers for electromagnetic, electrical, nuclear, or magnetic detection.

Caloric intake, physical activity, and metabolism can be monitored using a core temperature sensor, an accelerometer, a sound extraction methodology, a pulse oximeter, a hydration sensor, and the like. These sensors can be used individually or in unison to assess overall caloric metabolism and physical activity for purposes such as diet monitoring, exercise monitoring, athletic training, and the like. For example, a sound extraction methodology can be used to extract sounds associated with swallowing, and this can give an indication of total food volume consumed. Additionally, a core temperature sensor, such as a thermopile, a pyroelectric sensor, a thermoelectric sensor, or a thermistor, or a tympanic membrane extraction technique, can be used to assess metabolism. In one case, the core temperature is compared with the outdoor temperature, and an estimate of the heat loss from the body is made, which is related to metabolism.

Environmental temperature can be monitored, for example, by thermistor, thermocouple, diode junction drop reference, or the like. Electrical temperature measurement techniques are well known to those skilled in the art, and are of suitable size and power consumption that they can be integrated into a wireless earpiece module without significant impact on the size or functionality of the wireless earpiece module.

Environmental noise can be monitored, for example, by transducer, microphone, or the like. Monitoring of environmental noise preferably includes, but is not limited to, instantaneous intensity, spectral frequency, repetition frequency, peak intensity, commonly in units of decibels, and cumulative noise level exposures, commonly in units of decibel-hours. This environmental noise may or may not include noise generated by a person wearing an earpiece module. Sound made by a person wearing an earpiece module may be filtered out, for example, using analog or digital noise cancellation techniques, by directional microphone head shaping, or the like. The environmental noise sensor may or may not be the same sensor as that used for the intended purpose of wireless communication. In some embodiments, the environmental noise sensor is a separate sensor having broader audible detection range of noise level and frequency, at the possible sacrifice of audio quality.

Environmental smog includes VOCs, formaldehyde, alkenes, nitric oxide, PAH's, sulfur dioxide, carbon monoxide, olefins, aromatic compounds, xylene compounds, and the like. Monitoring of the aforementioned smog components can be performed using earpiece modules and other wearable apparatus, according to some embodiments of the present invention, and in a variety of methods. All smog components may be monitored. Alternatively, single smog components or combinations of smog components may be monitored. Photoionization detectors (PID's) may be used to provide continuous monitoring and instantaneous readings. Other methods of detecting smog components according to embodiments of the present invention include, but are not limited to, electrocatalytic, photocatalytic, photoelectrocatalytic, colorimetric, spectroscopic or chemical reaction methods. Examples of monitoring techniques using the aforementioned methods may include, but are not limited to, IR laser absorption spectroscopy, difference frequency generation laser spectroscopy, porous silicon optical microcavities, surface plasmon resonance, absorptive polymers, absorptive dielectrics, and colorimetric sensors. For example, absorptive polymer capacitors inductors, or other absorptive polymer-based electronics can be incorporated into an earpiece module (e.g., 10, FIG. 1) according to embodiments of the present invention. These polymers change size or electrical or optical properties in response to analyte(s) from the environment (such as those described above). The electrical signal from these absorptive polymer electronic sensors can be correlated with the type and intensity of environmental analyte. Other techniques or combinations of techniques may also be employed to monitor smog components. For example, a smog component may be monitored in addition to a reference, such as oxygen, nitrogen, hydrogen, or the like. Simultaneous monitoring of smog components with a reference analyte of known concentration allows for calibration of the estimated concentration of the smog component with respect to the reference analyte within the vicinity of an earpiece user.

In some embodiments of the present invention, environmental air particles can be monitored with a flow cell and a particle counter, particle sizer, particle identifier, or other particulate matter sensor incorporated as part of an earpiece module (e.g., 10, FIG. 1) or externally attached to an earpiece module. Non-limiting examples of particles include oil, metal shavings, dust, smoke, ash, mold, or other biological contaminates such as pollen. In some embodiments of the present invention, a sensor for monitoring particle size and concentration is an optical particle counter. A light source is used (e.g., a laser or a laser diode), to illuminate a stream of air flow. However, a directional LED beam, generated by a resonant cavity LED (RCLED), a specially lensed LED, or an intense LED point source, can also be used for particle detection. The optical detector which is off-axis from the light beam measures the amount of light scattered from a single particle by refraction and diffraction. Both the size and the number of particles can be measured at the same time. The size of the monitored particle is estimated by the intensity of the scattered light. Additionally, particles can be detected by ionization detection, as with a commercial ionization smoke detector. In this case, a low-level nuclear radiation source, such as americium-241, may be used to ionize particles in the air between two electrodes, and the total ionized charge is detected between the electrodes. As a further example, piezoelectric crystals and piezoelectric resonator devices can be used to monitor particles in that particles reaching the piezoelectric surface change the mass and hence frequency of electromechanical resonance, and this can be correlated with particle mass. If the resonators are coated with selective coatings, certain types of particles can attach preferentially to the resonator, facilitating the identification of certain types of particles in the air near a person wearing an earpiece module. In some embodiments, these resonators are solid state electrical devices, such as MEMS devices, thin film bulk acoustic resonators (FBARs), surface-acoustic wave (SAW) devices, or the like. These compact solid state components may be arrayed, each arrayed element having a different selective coating, for monitoring various types of particles.

In some embodiments of the present invention, environmental air pressure or barometric pressure can be monitored by a barometer. Non-limiting examples of barometric pressure measurement include hydrostatic columns using mercury, water, or the like, foil-based or semiconductor-based strain gauge, pressure transducers, or the like. In some embodiments of the present invention, semiconductor-based strain gauges are utilized. A strain gauge may utilize a piezoresistive material that gives an electrical response that is indicative of the amount of deflection or strain due to atmospheric pressure. Atmospheric pressure shows a diurnal cycle caused by global atmospheric tides. Environmental atmospheric pressure is of interest for prediction of weather and climate changes. Environmental pressure may also be used in conjunction with other sensing elements, such as temperature and humidity to calculate other environmental factors, such as dew point. Air pressure can also be measured by a compact MEMS device composed of a microscale diaphragm, where the diaphragm is displaced under differential pressure and this strain is monitored by the piezoelectric or piezoresistive effect.

In some embodiments of the present invention, environmental humidity, relative humidity, and dew point can be monitored by measuring capacitance, resistivity or thermal conductivity of materials exposed to the air, or by spectroscopy changes in the air itself. Resistive humidity sensors measure the change in electrical impedance of a hygroscopic medium such as a conductive polymer, salt, or treated substrate. Capacitive humidity sensors utilize incremental change in the dielectric constant of a dielectric, which is nearly directly proportional to the relative humidity of the surrounding environment. Thermal humidity sensors measure the absolute humidity by quantifying the difference between the thermal conductivity of dry air and that of air containing water vapor. Humidity data can be stored along with pressure monitor data, and a simple algorithm can be used to extrapolate the dew point. In some embodiments of the present invention, monitoring humidity is performed via spectroscopy. The absorption of light by water molecules in air is well known to those skilled in the art. The amount of absorption at known wavelengths is indicative of the humidity or relative humidity. Humidity may be monitored with a spectroscopic method that is compatible with the smog monitoring spectroscopic method described above.

When environmental factors such as the aforementioned are monitored continuously in real-time, a user's total exposure level to an environmental factor can be recorded. When a representative volume of air a user has been exposed to is monitored or estimated, the volumetric concentration of the analytes can be calculated or estimated. In order to estimate the volume of air a person wearing an earpiece has been exposed to, a pedometer or accelerometer or air flow sensor can also be integrated into an earpiece module. Pedometers and accelerometers can be integrated into an earpiece module via mechanical sensors (usually implementing a mechanical-electrical switch), MEMS devices, and/or gyroscopic technologies. The technologies required for these types of pedometers and accelerators are well known to those skilled in the art. The incorporated pedometer or accelerometer (or more than one pedometer or accelerometer) is used to gage the distance a person has traveled, for use in the estimation of the volume of air to which a person has been exposed, and the subsequent estimate of the volumetric concentration of monitored analytes.

The health and environmental sensors utilized with earpiece modules and other wearable monitoring apparatus, according to embodiments of the present invention, can operate through a user-selectable switch on an earpiece module. However, health and environmental sensors can also be run automatically and independently of the person wearing the apparatus. In other embodiments, the person may control health and environmental monitoring through a device wirelessly coupled to an earpiece module, such as a portable telecommunication device. For example, health and environmental sensors in or about an earpiece module can be controlled wirelessly through, for example, a cell phone, laptop, or personal digital assistant (PDA).

A wearable monitoring device 10 may be configured such that user preferences can be "downloaded" wirelessly without requiring changes to the earpiece monitor hardware. For example, an earpiece concerned about a heart condition may wish to have the signal processor 13 focus on processing pulse signature, at the expense of ignoring other physiological or environmental parameters. The user may then use the portable telecommunication device 22 to download a specialized algorithm through the web. This may be accomplished through existing wireless infrastructure by text-messaging to a database containing the algorithm. The user will then have an earpiece module suited with analysis software specialized to the needs and desires of the user.

Health and environmental monitors, according to embodiments of the present invention, enable low-cost, real-time personal health and environmental exposure assessment monitoring of various health factors. An individual's health and environmental exposure record can be provided throughout the day, week, month, or the like. Moreover, because the health and environmental sensors can be small and compact, the overall size of an apparatus, such as an earpiece, can remain lightweight and compact.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this That which is claimed is:

1. A wearable apparatus in a wrist-worn form factor that is configured to be worn on a wrist of a subject, the wearable apparatus comprising:
a photoplethysmography (PPG) sensor module comprising at least one optical emitter configured to emit optical energy and at least one optical detector configured to output signals responsive to the emitted optical energy, wherein the signals outputted by the at least one optical detector contain pulse rate data;
a motion sensor configured to obtain subject body motion information in real-time;
a plurality of physiological sensors configured to obtain physiological signals from the subject;
a wireless transmitter/receiver;
a power source;
at least one processor in communication with the PPG sensor module, the motion sensor, the plurality of physiological sensors, and the wireless transmitter/receiver, the at least one processor configured to:
receive and process the subject body motion information obtained by the motion sensor in real-time;
identify, based on the processed subject body motion information, footstep-related skin vibrations;
subtract, reduce or eliminate optical scatter associated with the identified footstep-related skin vibrations from the pulse rate data in the signals outputted by the at least one optical detector; and
a communication and entertainment module configured to provide pulse rate biofeedback to the subject, wherein the communication and entertainment module comprises at least one audio device configured to communicate with the subject via sound and at least one vibration device configured to communicate with the subject via physical actuation;
wherein the wireless transmitter/receiver is configured to transmit the pulse rate data of the subject to a device remotely located from the subject, and wirelessly download a user preference from the device to the wearable apparatus, and
wherein the at least one processor is configured to process the physiological signals obtained by the plurality of physiological sensors, and focus signal processing resources on extracting physiological information from the physiological signals obtained by one or more of the plurality of physiological sensors based on the user preference.

2. The wearable apparatus of claim 1, wherein the at least one processor is configured to process the pulse rate data of the subject into pulse signals that can be viewed by the subject via a user interface.

3. The wearable apparatus of claim 2, wherein the wireless transmitter/receiver is configured to transmit the pulse signals processed from the pulse rate data of the subject to a device remotely located from the subject.

4. The wearable apparatus of claim 1, wherein the motion sensor is an accelerometer, a gyroscope, or a MEMS sensor.

5. The wearable apparatus of claim 1, further comprising at least one environmental sensor configured to sense environmental information in a vicinity of the subject, and wherein the at least one processor is configured to assess a health state of the subject using the pulse rate data and the environmental information.

6. The wearable apparatus of claim 1, further comprising a data storage and wherein the transmitter/receiver is configured to wirelessly upload at least one algorithm to the data storage.

7. The wearable apparatus of claim 1, further comprising an ultraviolet (UV) sensor configured to detect exposure of the subject to UV radiation.

8. The wearable apparatus of claim 1, wherein the communication and entertainment module is further configured to present visible information to the subject.

9. The wearable apparatus of claim 1, wherein the apparatus is a wrist-watch.

10. The wearable apparatus of claim 1, wherein the at least one processor is further configured to store the pulse rate data of the subject in a remote database, wherein the pulse rate data stored in the remote database is accessible via a user interface, and
wherein the remote database is configured to:
identify data corrupted by motion artifacts in the stored pulse rate data based on a history of measured physiological and/or environmental data; and
extract physiological information and/or environmental information from the corrupted data.

11. The wearable apparatus of claim 1, wherein the at least one processor is further configured to analyze the pulse rate data in context with the subject body motion information to identify one or more health issues associated with the subject.

12. A system, comprising:
a wearable device in a wrist-worn form factor that is configured to be worn on a wrist of a subject, the wearable device comprising:
a photoplethysmography (PPG) sensor module comprising at least one optical emitter configured to emit optical energy and at least one optical detector configured to output signals responsive to the emitted optical energy, wherein the signals outputted by the at least one optical detector contain pulse rate data;
a motion sensor configured to obtain subject body motion information in real-time;
at least one environmental sensor configured to sense environmental information in a vicinity of the subject and output environmental signals responsive thereto;
a wireless transmitter/receiver;
a power source;
at least one processor in communication with the PPG sensor module, the motion sensor, the at least one environmental sensor, and the wireless transmitter/receiver, the at least one processor configured to:
receive and process the environmental signals outputted by the at least one environmental sensor in real-time to identify the environmental information;
receive and process the subject body motion information obtained by the motion sensor in real-time;
identify, based on the processed subject body motion information, footstep-related skin vibrations; and
subtract, reduce or eliminate optical scatter associated with the identified footstep-related skin vibrations from the pulse rate data in the signals outputted by the at least one optical detector; and
a communication and entertainment module configured to provide pulse rate biofeedback to the subject, wherein the communication and entertainment module comprises at least one audio device configured to communicate with the subject via sound and at least one vibration device configured to communicate with the subject via physical actuation; and a device remotely located from the subject, wherein the wireless transmitter/receiver is configured to transmit the pulse rate data of the subject to the device, and wherein the wireless transmitter/receiver is configured to wirelessly download a user preference from the device to the wearable device, wherein the at least one processor is configured to prioritize signal processing resources on processing the pulse rate data over processing the environmental information of the at least one environmental sensor in response to the user preference.

13. The system of claim 12, wherein the wearable device comprises a display, and wherein the wearable device is configured to process the pulse rate data of the subject into signals that can be viewed by the subject via the display.

14. The system of claim 12, further comprising a remote database, wherein the wearable device is configured to store the pulse rate data of the subject in the remote database, and wherein the pulse rate data stored in the remote database is accessible via a user interface.

15. The system of claim 14, wherein the remote database is configured to allow the subject to compare his/her pulse rate data with pulse rate data stored in the remote database of others in selected demographics.

16. The system of claim 15, wherein the remote database is configured to provide a graphical comparison between the pulse rate data of the subject and pulse rate data of others in selected demographics.

17. The system of claim 14, wherein the remote database is configured to:
identify data corrupted by motion artifacts in the stored pulse rate data based on a history of measured physiological and/or environmental data; and
extract physiological information and/or the environmental information from the corrupted data.

18. The system of claim 12, wherein the at least one processor is further configured to analyze the pulse rate data in context with the subject body motion information to identify one or more health issues associated with the subject.

19. The system of claim 12, wherein the at least one processor is further configured to analyze the pulse rate data in context with the subject body motion information to determine a stress level of the subject and to identify a source of stress.

20. A wearable apparatus in a wrist-worn form factor that is configured to be worn on a wrist of a subject, the wearable apparatus comprising:
a photoplethysmography (PPG) sensor module comprising at least one optical emitter and at least one optical detector, wherein signals outputted by the at least one optical detector contain pulse rate data;
a motion sensor configured to obtain subject body motion information in real-time;
at least one environmental sensor configured to sense environmental information in a vicinity of the subject; and
at least one processor in communication with the PPG sensor module, the motion sensor, and the at least one environmental sensor, the at least one processor configured to:
remove body motion artifacts from the pulse rate data in real time through dynamic feedback from the motion sensor;
determine a stress level of the subject using the pulse rate data, the subject body motion information, and the environmental information;
identify a source of stress that is associated with the environmental information in the vicinity of the subject;
determine a location of the wearable apparatus; and
identify a geographic location of the source of stress based on a time-dependent analysis of the pulse rate data, the determined location of the wearable apparatus, and the environmental information in the vicinity of the subject.

21. A system, comprising:
a remote database; and
a wearable apparatus in a wrist-worn form factor that is configured to be worn on a wrist of a subject, the wearable apparatus comprising:
a photoplethysmography (PPG) sensor module comprising at least one optical emitter configured to emit optical energy and at least one optical detector configured to output signals responsive to the emitted optical energy, wherein the signals outputted by the at least one optical detector contain pulse rate data;
a motion sensor configured to obtain subject body motion information in real-time;
a wireless transmitter/receiver;
a power source;
at least one processor in communication with the PPG sensor module, the motion sensor, and the wireless transmitter/receiver, the at least one processor configured to:
receive and process the subject body motion information obtained by the motion sensor in real-time;
identify, based on the processed subject body motion information, footstep-related skin vibrations;
subtract, reduce or eliminate optical scatter associated with the identified footstep-related skin vibrations from the pulse rate data in the signals outputted by the at least one optical detector; and
store the pulse rate data in the remote database, wherein the pulse rate data stored in the remote database is accessible via a user interface; and
a communication and entertainment module configured to provide pulse rate biofeedback to alert the subject if the subject is meeting one or more physiological targets or exceeding one or more safe physiological limits, wherein the communication and entertainment module comprises at least one audio device configured to communicate with the subject via sound and at least one vibration device configured to communicate with the subject via physical actuation;
wherein the remote database is configured to:
identify data corrupted by motion artifacts in the stored pulse rate data based on a history of measured physiological and/or environmental data; and
extract physiological information and/or environmental information from the corrupted data.

* * * * *